United States Patent
Coia et al.

(10) Patent No.: US 6,562,622 B1
(45) Date of Patent: May 13, 2003

(54) CONTINUOUS IN VITRO EVOLUTION

(75) Inventors: Gregory Coia, Brunswick Victoria (AU); Peter John Hudson, Blackburn Victoria (AU); Peter Iliades, North Balwyn Victoria (AU); Robert Alexander Irving, Mulgrave Victoria (AU)

(73) Assignee: Diatech PTY, LTD (AU)

( * ) Notice: Subject to any disclaimer, the term of this patent is extended or adjusted under 35 U.S.C. 154(b) by 0 days.

(21) Appl. No.: 09/674,677

(22) PCT Filed: May 7, 1997

(86) PCT No.: PCT/AU99/00341

§ 371 (c)(1),
(2), (4) Date: Dec. 11, 2000

(87) PCT Pub. No.: WO99/58661

PCT Pub. Date: Nov. 18, 1999

(30) Foreign Application Priority Data

May 8, 1998 (AU) .............................................. PP3445

(51) Int. Cl.[7] .......................... C12N 15/00; C12Q 1/00; C12Q 1/68

(52) U.S. Cl. ................................ 435/440; 435/4; 435/6

(58) Field of Search .............................. 536/23.1, 24.1, 536/23.5, 24.2, 24.5; 435/320.1, 252.1, 325, 183, 405, 440, 4, 6; 530/350, 387.1, 402

(56) References Cited

U.S. PATENT DOCUMENTS

| | | |
|---|---|---|
| 5,556,769 A | 9/1996 | Wu et al. |
| 5,602,001 A | 2/1997 | Kramer et al. |
| 5,643,768 A | 7/1997 | Kawasaki |

FOREIGN PATENT DOCUMENTS

| | | | |
|---|---|---|---|
| WO | WO-9105058 | * | 10/1989 |
| WO | WO 94/06928 | | 3/1994 |

OTHER PUBLICATIONS

Brian K. Davis, Kinetics of Rapid RNA Evolution in Vitro, Journal If Molecular Evolution, (1991) 33, pp. 343–356.*
Christof K. Biebricher et al., Sequence Analysis of RNA Species Synthesized by QB Replicase without Template, Biochemistry, 1993, 32, pp. 4848–4854.*
Kenneth W. Walker et al., Effect of Redox Enviroment on the in Vitro and in Vivo Folding of RTEM–1 B–Lactamase and Escherichia coli Alkaline Phosphatase, The Journal of Biological Chemistry, vol. 269, No. 45, pp. 28487–28493.*
David Brown et al., Template Recognition by an RNA–Dependent RNA Polymerase: Identification and Characterization of Two RNA Binding Sites on QB Replicase, Biochemistry, 1995, 34, pp. 14765–14774.*
Mark D. Moody et al., Evolution of Host Cell RNA into Efficient Template RNA by QB Replicase: The Origin of RNA in Untemplated Reactions, Biochemistry 1994, 33, pp. 13836–13847.*
Lubov Ryabova et al., Coupled Replication–Translation of Amplifiable Messenger RNA, The Journal of Biological Chemistry, vol. 269, No. 2, pp. 1501–1505.*
PROMEGA, In Vitro Resource, pp. 63–67.*
Paul m. Lizardi et al., Exponential Amplification of Recombinant—RNA Hybridization Probes, Bio/Technology, vol. 6, pp. 1197–1202.*
Lecture Outlines 2000, Biology 403, Molecular Biology, pp. 1–6.*
Burton and Barbas (1994) Adv. in Immunology, 57:191–280.
Kolosov et al. (1992) Biotech. and Appl. Biochem., 16:125–133.
Ratten et al. (1990) Tibtech, 8:275–276.
Spririn (1990b) pp. 56–70 in "The Ribosome: Structure, Furnction and Evolution" (Ed. Hill et al.) Amer. Soc. Microbiol., Washington, D.C.
Spirin (1991) pp. 31–43 in "Frontiers in Bioprocessing II" (Ed. Todd et al.) Amer. Chem. Soc., Washington, D.C.
Zubay (1973) Ann. Rev. Genetics, 7:267–287.
Baranov et al. (1989). Gene 84:463–466.
Barrera et al. (1993). J. Mol. Biol. 232, 512–521.
Brown and Gold (1995a). Biochemistry 34, 14775–14782.
Brown and Gold (1995b). Biochemistry 34, 14765–14774.
Coia et al. (1996). J. Immunol. Meth. 192, 13–23.
Deiman et al (1997), J. Virol. 71, 5990–5996.
Duenas and Borrebaeck (1994). Bio/Technology 12, 999–1002.

(List continued on next page.)

Primary Examiner—Sean McGarry
Assistant Examiner—Mary Schmidt
(74) Attorney, Agent, or Firm—Frommer Lawrence & Haug; Thomas J. Kowalski

(57) ABSTRACT

The present invention provides a method for the mutation, synthesis and selection of a protein which binds to a target molecule, the method comprising: (a) incubating a replicable mRNA molecule encoding the protein with ribonucleoside triphosphate precursors of RNA and an RNA-directed RNA polymerase, wherein the RNA-directed RNA polymerase replicates the mRNA molecule but introduces mutations thereby generating a population of mutant mRNA molecules; (b) incubating the mutant mRNA molecules from step (a) with a translation system under conditions which results in the synthesis of population of mutant proteins such that after translation, mutant proteins are linked to their encoding mRNA molecules thereby forming a population of mutant proteins such that after translation, mutant proteins are linked to their encoding mRNA molecules thereby forming a population of mutant protein/mRNA complexes; (c) selecting one or more mutant protein/mRNA complex(es) by exposing the population of mutant protein/mRNA complexes from step (b) to the target molecule and recovering the mutant protein/mRNA complex(es) bound thereto.

38 Claims, 22 Drawing Sheets

OTHER PUBLICATIONS

Gram et al. (1992). PNAS 89, 3576–3580.
Hanes and Pluckthun (1997). Proc. Natl. Acad. Sci. (USA) 94, 4937–4942.
He and Taussig (1997). Nucleic Acids Research 25, 5132–5134.
Irving et al (1996). Immunotechnology 2, 127–143.
Keiler et al. (1996). Science 271, 990–993.
Kigawa et al. (1991). J. Biochem. 110, 166–168.
Kramer et al. (1978). Proc. Natl. Acad. Sci. (USA) 75, 5334–5338.
Krebber et al. (1995). FEBS Lett. 377, 227–231.
Krieg et al. (1984). Nucleic Acid Res. 12: 7057–7070.
Kudlicki et al. (1992). Analytical Biochemistry 206, 389–393.
Mattheakis et al. (1994). Proc. Natl. Acad. Sci. (USA) 91, 9022–9026.
Melton et al. (1984). Necleic Acid Res. 12: 7035–56.
Munishkin et al. (1991). J. Mol. Biol. 221, 463–472.
Nishihara et al. (1983). J.Biochem. (Tokyo) 93, 669–674.
Ojala PM and Bamford DH (1995) Virology, 207, 400–408.
Ryabova et al. (1989). Nucleic Acids Research 17, 4412.
Ryabova et al. (1997) Nature Biotech. 15, 79–84.
Spirin et al. (1988). Science 242, 1162–1164.
Stemmer (1994). Nature 370, 389–391.
Stemmer et al. (1995). Science 270, 1510.
Sumper and Luce (1975). Proc.Natl. Acad. Sci. (USA) 72, 162–166.
Tan et al. (1996). J. Mol. Biol. 261, 222–230.
Winter et al. (1994). Ann. Rev. Biochem. 12, 433.
Yang et al (1995). J Mol Biol 254, 392–403.
Zamora et al. (1995) Biochemistry 34, 12611–1266.
Zuker et al (1991) Nucleic Acids Res 19; 2707–14.
Proc. Natl. Acad Sci. 93, pp. 11558–11562 (1996) Brown et al. "RNA replication by Qβ replicase : A working model".
J. Biol. Chem 269(2), pp. 1501–1505 (1994) Ryabova L. et al "Coupled replication–translation of amplifiable mRNA".
Proc. Natl. Acad. Sci. 90, pp. 9325–2329 (1993) Morozov, I. Y. et al. "Synergism in replication and translation of mRNA in a cell free system.".
J. Mol. Biol. 249, pp. 756–762 (1995) Rohde, N et al. "The Mutant distribution of an RNA species replicated by Qβ replicase.".
Biophys. Chem. 66, pp. 179–192 (1997) Biebricher, C.K. and Gardiner, W.C. "Molecular evolution of RNA in vitro".

* cited by examiner

Figure 3: Continuous In Vitro Evolution

Figure 5

Figure 5(a) Sequence of Constant Light Region of mouse monoclonal 1C3
GCTGATGCTGCACCAACTGTATCCATCTTCCCACCATCCAGTGAGCAGTTAACATCTGGA
GGTGCCTCAGTCGTGTGCTTCTTGAACAACTTCTACCCCAAAGACATCAATGTCAAGTGG
AAGATTGATGGCAGTGAACGACAAAATGGCGTCCTGAACAGTTGGACTGATCAGGACAG
CAAAGACAGCACCTACAGCATGAGCAGCACCCTCACGTTGACCAAGGACGAGTATGAAC
GACATAACAGCTATACCTGTGAGGCCACTCACAAGACATCAACTTCACCCATTGTCAAGA
GCTTCAACAGGGGAGAGTGT Figure 5(b) Sequence of Human Constant Heavy Chain
GCAGATCAAGACACAGCCATCCGGGTCTTCGCCATCCCCCCATCCTTTGCCAGCATCTTC
CTCACCAAGTCCACCAAGTTGACCTGCCTGGTCACAGACCTGACCACCTATGACAGCGT
GACCATCTCCTGGACCCGCCAGAATGGCGAAGCTGTGAAAACCCACACCAACATCTCCG
AGAGCCACCCCAATGCCACTTTCAGCGCCGTGGGTGAGGCCAGCATCTGCGAGGATGA
CTGGAATTCCGGGGAGAGGTTCACGTGCACCGTGACCCACACAGACCTGCCCTCGCCAC
TGAAGCAGACCATCTCCCGGCCCAAGGGC Figure 5(c) Sequence of the anti-glycophorin (1C3) scFv
ATGGCCGAGGTGAGGCTTCTTGAGTCTGGAGGTGGCCCGGTACAACCTGGAGGATCCC
TGAAACTCTCCTGTGCAGCCTCAGGATTCGATTTTAGTAGATACTGGATGAATTGGGTCC
GGCGGGCTCCAGGGAAGGGGCTAGAGTGGATTGGAGAAATTAATCAACAAAGCAGTAC
GATAAACTATTCGCCACCTCTGAAGGATAAATTCATCATCTCCAGAGACAACGCCAAAAGT
ACGCTGTACCTGCAAATGAACAAAGTGAGATCTGAGGACACAGCCCTTTATTATTGTGCA
AGACTTTCTCTTACTGCGGCAGGGTTTGCTTACTGGGGCCAAGGGACTCTGGTCACCGT
CGCCTCCGGTGGTGGTGGTTCAGGAGGAGGAGGTTCGGGTGGTGGTGGTTCGGACATC
GTCATGTCACAGTCTCCATCCTCCCTGGCTGTGTCAGTAGGAGAGAAGGTCACTATGAG
CTGCAGATCCAGTCAGAGTCTGTTCAACAGTAGAACCCGAAAGAACTACTTGACTTGGTA
CCAGCAGAAACCAGGGCAGTCTCCTAAACCGCTGATCTACTGGGCATCCACTAGGGAAT
CTGGGGTCCCTGATCGCTTCACAGGCAGTGGATCTGGGACAGATTTCACTCTCACCATC
AGCAGTGTGCAGGCTGAAGACCTGGCAGATTATTACTGCAAGCAATCTTATAATCTTCGG
ACGTTCGGTGGAGGCACCAAGCTGGAAATCAAACGGG

Figure 5

Figure 5(d) Sequence of the anti-Hepatitis Surface antigen (4C2) scFv

CCATGGCCGATGTGAAGCTTCAGGAGTCAGGGCCTGAGCTGGTGAGGCCCGGGGTCTC
AGTGAAGATTACCTGCAAGGGTTCCGGCTACACATTCACTGATTATGCTATGCATTGGGT
GAAGCAGAGTCATGCCAAGAGTCTAGAGTGGATTGGACTTATTAGTAATTCCTTTGGTAA
TACAAACTACAACCAGAAGTTTGAGGCCAAGGCCACAATGACTGTAGACAAATCCTCCAA
CACAGGCTATTTGGAACTTGGCAGATTGACATCTGAGGATTCTGCCATCTATTACTGTGC
AAGAGTGATCGACTGGTCCTTCGATGTCTGGGGCCAAGGGACCACGGTCACCGTCTCCT
CAGGTGGAGGCGGTTCAGGCGGAGGTGGCTCTGGCGGTGGCGGATCGGACATTGTGC
TGACCCAATCTCCAGCAATCATGTTCGCATCTCCAGGGGAGAAGGTCACCATGACCTGCA
GTGCCAACTCACGTGTCAGGTACGTGCACTGGTACCAACAGAAGTCAGGCACCTCCCCC
AAAAGATGGATTTATGACACATCCAAACTGGCTTCTGGAGTCCCTGCTCGCTTCAGTGGC
AGTGGGTCTGGGACCTCTCACTCTCTCACAATCAGCAGCTTGGAGGCTGAAGATGCTGC
CACTTATTACTGCCAGCACTGGAGTAGTAACCCTCCCACGTTCGGTGCTGGGACCAAGCT
GGAAATAAAACGGGCGGCCGCAGATTATAAAGATGATGATGATAAAGCCGCGGCCCATC
ACCACCATCACCATTAAGAATTCAGCCCGCCTAATG

Figure 6a

```
GGGGACCCCCTTTAGGGGGTCACCTCACACAGCAGTACTTCACTGAGTATAAGAGGACA
TATGCCTAAATTACCGCGTGGTCTGCGTTTCGGAGCCGATAATGAAATTCTTAATGATTTT
CAGGAGCTCTGGTTTCCAGACCTCTTTATCGAATCTTCCGACACGCATCCGTGGTACACA
CTGAAGGGTCGTGTGTTGAACGCCCACCTTGATGATCGTCTACCTAATGTAGGCGGTCG
CCAGGTAAGGCGCACTCCACATCGCGTCACCGTTCCGATTGCCTCTTCAGGCCTTCGTC
CGGTAACAACCGTTCAGTATGATCCCGCAGCACTATCGTTCTTATTGAACGCTCGTGTTG
ACTGGGATTTCGGTAATGGCGATAGTGCGAACCTTGTCATTAATGACTTTCTGTTTCGCA
CCTTTGCACCTAAGGAGTTTGATTTTTCGAACTCCTTAGTTCCTCGTTATACTCAGGCCTT
CTCCGCGTTTAATGCCAAGTATGGCACTATGATCGGCGAAGGGCTCGAGACTATAAAATA
TCTCGGGCTTTTACTGCGCAGACTGCGTGAGGGTTACGCGCTGTTAAGCGTGGCGATT
TACGTGCTCTTCGTAGGGTTATCCAGTCCTACCATAATGGTAAGTGGAAACCGGCTACTG
CTGGTAATCTCTGGCTTGAATTTCGTTATGGCCTTATGCCTCTCTTTTATGACATCAGAGA
TGTCATGTTAGACTGGCAGAACCGTCATGATAAGATTCAACGCCTCCTTCGGTTTTCTGTT
GGTCACGGCGAGGATTACGTTGTCGAATTCGACAATCTGTACCCTGCCGTTGCTTACTTT
AAACTGAAAGGGGAGATTACACTCGAACGCCGTCATCGTCATGGCATATCTTACGCTAAC
CGCGAAGGATATGCTGTTTTCGACAACGGTTCCCTTCGGCCTGTGTCCGATTGGAAGGA
GCTTGCCACTGCATTCATCAATCCGCATGAAGTTGCTTGGGAGTTAACTCCCTACAGCTT
CGTTGTTGATTGGTTCTTGAATGTTGGTGACATACTTGCTCAACAAGGTCAGCTATATCAT
AATATCGATATTGTAGACGGCTTTGACAGACGTGACATCCGGCTCAAATCTTTCACCATAA
AAGGTGAACGAAATGGGCGGCCTGTTAACGTTTCTGCTAGCCTGTCTGCTGTCGATTTAT
TTTACAGCCGACTCCATACGAGCAATCTTCCGTTCGCTACACTAGATCTTGATACTACCTT
TAGTTCGTTTAAACACGTTCTTGATAGTATCTTTTTATTAACCCAACGCGTAAAGCGTTGA
AACTTTGGGTCAATTTGATCATGGCAAAATTAGAGACTGTTACTTTAGGTAACATCGGGAA
AGATGGAAAACAAACTCTGGTCCTCAATCCGCGTGGGGTAAATCCCACTAACGGCGTTG
CCTCGCTTTCACAAGCGGGTGCAGTTCCTGCGCTGGAGAAGCGTGTTACCGTTTCGGTA
TCTCAGCCTTCTCGCAATCGTAAGAACTACAAGGTCCAGGTTAAGATCCAGAACCCGACC
GCTTGCACTGCAAACGGTTCTTGTGACCCATCCGTTACTCGCCAGGCATATGCTGACGTG
ACCTTTTCGTTCACGCAGTATAGTACCGATGAGGAACGAGCTTTTGTTCGTACAGAGCTT
GCTGCTCTGCTCGCTAGTCCTCTGCTGATCGATGCTATTGATCAGCTGAACCCAGCGTAT
TGAACACTGCTCATTGCCGGTGGTGGCTCAGGGTCAAAACCCGATCCGGTTATTCCGGA
TCCACCGATTGATCCGCCGCCAGGGACAGGTAAGTATACCTGTCCCTTCGCAATTTGGTC
CCTAGAGGAGGTTTACGAGCCTCCTACTAAGAACCGACCGTGGCCTATCTATAATGCTGT
TGAACTCCAGCCTCGCGAATTTGATGTTGCCCTCAAAGATCTTTTGGGCAATACAAAGTG
GCGTGATTGGGATTCTCGGCTTAGTTATACCACGTTCCGCGGTTGCCGTGGCAATGGTT
ATATTGACCTTGATGCGACTTATCTTGCTACTGATCAGGCTATGCGTGATCAGAAGTATGA
```

Figure 6b

| | Figure 6a |
| Figure 6 | Figure 6b |
| | Figure 6c |
| | Figure 6d |

```
TATTCGCGAGGGCAAGAAACCTGGTGCTTTCGGTAACATTGAGCGATTCATTTATCTTAA
GTCGATAAATGCTTATTGCTCTCTTAGCGATATTGCGGCCTATCACGCCGATGGCGTGAT
AGTTGGCTTTTGGCGCGATCCATCCAGTGGTGGTGCCATACCGTTTGACTTCACTAAGTT
TGATAAGACTAAATGTCCTATTCAAGCCGTGATAGTCGTTCCTCGTGCTTAGTAACTAAGG
ATGAAATGCATGTCTAAGACAGCATCTTCGCGTAACTCTCTCAGCGCACAATTGCGCCGA
GCCGCGAACACAAGAATTGAGGTTGAAGGTAACCTCGCACTTTCCATTGCCAACGATTTA
CTGTTGGCCTATGGTCAGTCGCCATTTAACTCTGAGGCTGAGTGTATTTCATTCAGCCCG
AGATTCGACGGGACCCCGGATGACTTTAGGATAAATTATCTTAAAGCCGAGATCATGTCG
AAGTATGACGACTTCAGCCTAGGTATTGATACCGAAGCTGTTGCCTGGGAGAAGTTCCTG
GCAGCAGAGGCTGAATGTGCTTTAACGAACGCTCGTCTCTATAGGCCTGACTACAGTGA
GGATTTCAATTTCTCACTGGGCGAGTCATGTATACACATGGCTCGTAGAAAAATAGCCAA
GCTAATAGGAGATGTTCCGTCCGTTGAGGGTATGTTGCGTCACTGCCGATTTTCTGGCG
GTGCTACAACAACGAATAACCGTTCGTACGGTCATCCGTCCTTCAAGTTTGCGCTTCCGC
AAGCGTGTACGCCTCGGGCTTTGAAGTATGTTTTAGCTCTCAGAGCTTCTACACATTTCG
ATATCAGAATTTCTGATATTAGCCCTTTTAATAAAGCAGTTACTGTACCTAAGAACAGTAA
GACAGATCGTTGTATTGCTATCGAACCTGGTTGGAATATGTTTTTCCAACTGGGTATCGG
TGGCATTCTACGCGATCGGTTGCGTTGCTGGGGTATCGATCTGAATGATCAGACGATAAA
TCAGCGCCGCGCTCACGAAGGCTCCGTTACTAATAACTTAGCAACGGTTGATCTCTCAGC
GGCAAGCGATTCTATATCTCTTGCCCTCTGTGAGCTCTTATTGCCCCAGGCTGGTTTGA
GGTTCTTATGGACCTCAGATCACCTAAGGGGCGATTGCCTGACGGTAGTGTTGTTACCTA
CGAGAAGATTTCTTCTATGGGTAACGGTTACACATTCGAGCTCGAGTCGCTTATTTTTGCT
TCTCTCGCTCGTTCCGTTTGTGAGATACTGGACTTAGACTCGTCTGAGGTCACTGTTTAC
GGAGACGATATTATTTTACCGTCCTGTGCAGTCCCTGCCCTCCGGGAAGTTTTTAAGTAT
GTTGGTTTTACGACCAATACTAAAAAGACTTTTTCCGAGGGGCCGTTCAGAGAGTCGTGC
GGCAAGCACTACTATTCTGGCGTAGATGTTACTCCCTTTTACATACGTCACCGTATAGTGA
GTCCTGCCGATTTAATACTGGTTTTGAATAACCTATATCGGTGGGCCACAATTGACGGCG
TATGGGATCCTAGGGCCCATTCTGTGTACCTCAAGTATCGTAAGTTGCTGCCTAAACAGC
TGCAACGTAATACTATACCTGATGGTTACGGTGATGGTGCCCTCGTCGGATCGGTCCTAA
TCAATCCTTTCGCGAAAAACCGCGGGTGGATCCGGTACGTACCGGTGATTACGGACCAT
ACAAGGGACCGAGAGCGCGCTGAGTTGGGGTCGTATCTCTACGACCTCTTCTCGCGTTG
TCTCTCGGAAAGTAACGATGGGTTGCCTCTTAGGGGTCCATCGGGTTGCGATTCTGCGG
ATCTATTTGCCATCGATCAGCTTATCTGTAGGAGTAATCCTACGAAGATAAGCAGGTCTAC
CGGCAAATTCGATATACAGTATATCGCGTGCAGTAGCCGTGTTCTGGCACCCTACGGGG
TCTTCCAGGGCACGAAGGTTGCGTCTACACGAGGCGTAACCTGGGAGGGCGCCAATA
TGGCGCCTAATTGTGAATAAATTATCACAATTACTCTTACGAGTGAGAGGGGGATCTGCT
TTGCCCTCTCTCCTCCCGGGGATCCACTAGTTCTAGGTACTCGGGCAGCGTTGGGTCC
TGGCCACGGGTGCGCATGATCGTGCTCCTGTCGTTGAGGACCCGGCTAGGCTGGCGGG
GTTGCCTTACTGGTTAGCAGAATGAATCACCGATACGCGAGCGAACGTGAAGCGACTGC
```

Figure 6c

| | Figure 6a |
| Figure 6 | Figure 6b |
| | Figure 6c |
| | Figure 6d |

Figure 6c

```
TGCTGCAAAACGTCTGCGACCTGAGCAACAACATGAATGGTCTTCGGTTTCCGTGTTTCG
TAAAGTCTGGAAACGCGGAAGTCAGCGCCCTGCACCATTATGTTCCGGATCTGCATCGC
AGGATGCTGCTGGCTACCCTGTGGAACACCTACATCTGTATTAACGAAGCGCTGGCATTG
ACCCTGAGTGATTTTTCTCTGGTCCCGCCGCATCCATACCGCCAGTTGTTTACCCTCACA
ACGTTCCAGTAACCGGGCATGTTCATCATCAGTAACCCGTATCGTGAGCATCCTCTCTCG
TTTCATCGGTATCATTACCCCCATGAACAGAAATTCCCCCTTACACGGAGGCATCAAGTG
ACCAAACAGGAAAAAACCGCCCTTAACATGGCCCGCTTTATCAGAAGCCAGACATTAACG
CTTCTGGAGAAACTCAACGAGCTGGACGCGGATGAACAGGCAGACATCTGTGAATCGCT
TCACGACCACGCTGATGAGCTTTACCGCAGCTGCCTCGCGCGTTTCGGTGATGACGGTG
AAAACCTCTGACACATGCAGCTCCCGGAGACGGTCACAGCTTGTCTGTAAGCGGATGCC
GGGAGCAGACAAGCCCGTCAGGGCGCGTCAGCGGGTGTTGGCGGGTGTCGGGGCGCA
GCCATGACCCAGTCACGTAGCGATAGCGGAGTGTATACTGGCTTAACTATGCGGCATCA
GAGCAGATTGTACTGAGAGTGCACCATATGCGGTGTGAAATACCGCACAGATGCGTAAG
GAGAAAATACCGCATCAGGCGCTCTTCCGCTTCCTCGCTCACTGACTCGCTGCGCTCGG
TCGTTCGGCTGCGGCGAGCGGTATCAGCTCACTCAAAGGCGGTAATACGGTTATCCACA
GAATCAGGGGATAACGCAGGAAAGAACATGTGAGCAAAAGGCCAGCAAAAGGCCAGGAA
CCGTAAAAAGGCCGCGTTGCTGGCGTTTTTCCATAGGCTCCGCCCCCTGACGAGCATC
ACAAAAATCGACGCTCAAGTCAGAGGTGGCGAAACCCGACAGGACTATAAAGATACCAG
GCGTTTCCCCCTGGAAGCTCCCTCGTGCGCTCTCCTGTTCCGACCCTGCCGCTTACCGG
ATACCTGTCCGCCTTTCTCCCTTCGGGAAGCGTGGCGCTTTCTCATAGCTCACGCTGTAG
GTATCTCAGTTCGGTGTAGGTCGTTCGCTCCAAGCTGGGCTGTGTGCACGAACCCCCCG
TTCAGCCCGACCGCTGCGCCTTATCCGGTAACTATCGTCTTGAGTCCAACCCGGTAAGAC
ACGACTTATCGCCACTGGCAGCAGCCACTGGTAACAGGATTAGCAGAGCGAGGTATGTA
GGCGGTGCTACAGAGTTCTTGAAGTGGTGGCCTAACTACGGCTACACTAGAAGGACAGT
ATTTGGTATCTGCGCTCTGCTGAAGCCAGTTACCTTCGGAAAAAGAGTTGGTAGCTCTTG
ATCCGGCAAACAAACCACCGCTGGTAGCGGTGGTTTTTTTGTTGCAAGCAGCAGATTAC
GCGCAGAAAAAAAGGATCTCAAGAAGATCCTTTGATCTTTTCTACGGGGTCTGACGCTCA
GTGGAACGAAAACTCACGTTAAGGGATTTTGGTCATGAGATTATCAAAAAGGATCTTCAC
CTAGATCCTTTTAAATTAAAAATGAAGTTTTAAATCAATCTAAAGTATATATGAGTAAACTT
GGTCTGACAGTTACCAATGCTTAATCAGTGAGGCACCTATCTCAGCGATCTGTCTATTTC
GTTCATCCATAGTTGCCTGACTCCCCGTCGTGTAGATAACTACGATACGGGAGGGCTTAC
CATCTGGCCCCAGTGCTGCAATGATACCGCGAGACCCACGCTCACCGGCTCCAGATTTA
TCAGCAATAAACCAGCCAGCCGGAAGGGCCGAGCGCAGAAGTGGTCCTGCAACTTTATC
CGCCTCCATCCAGTCTATTAATTGTTGCCGGGAAGCTAGAGTAAGTAGTTCGCCAGTTAA
TAGTTTGCGCAACGTTGTTGCCATTGCTGCAGGCATCGTGGTGTCACGCTCGTCGTTTG
GTATGGCTTCATTCAGCTCCGGTTCCCAACGATCAAGGCGAGTTACATGATCCCCCATGT
TGTGCAAAAAAGCGGTTAGCTCCTTCGGTCCTCCGATCGTTGTCAGAAGTAAGTTGGCC
GCAGTGTTATCACTCATGGTTATGGCAGCACTGCATAATTCTCTTACTGTCATGCCATCCG
```

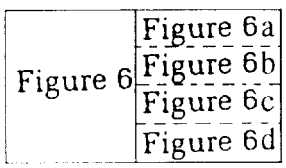

Figure 6d

```
TAAGATGCTTTTCTGTGACTGGTGAGTACTCAACCAAGTCATTCTGAGAATAGTGTATGC
GGCGACCGAGTTGCTCTTGCCCGGCGTCAACACGGGATAATACCGCGCCACATAGCAGA
ACTTTAAAAGTGCTCATCATTGGAAAACGTTCTTCGGGGCGAAAACTCTCAAGGATCTTAC
CGCTGTTGAGATCCAGTTCGATGTAACCCACTCGTGCACCCAACTGATCTTCAGCATCTT
TTACTTTCACCAGCGTTTCTGGGTGAGCAAAAACAGGAAGGCAAAATGCCGCAAAAAAGG
GAATAAGGGCGACACGGAAATGTTGAATACTCATACTCTTCCTTTTTCAATATTATTGAAG
CATTTATCAGGGTTATTGTCTCATGAGCGGATACATATTTGAATGTATTTAGAAAAATAAA
CAAATAGGGGTTCCGCGCACATTTCCCCGAAAAGTGCCACCTGACGTCTAAGAAACCATT
ATTATCATGACATTAACCTATAAAAATAGGCGTATCACGAGGCCCTTTCGTCTTCAAGAAT
TGGCGAACGTGGCGAGAAAGGAAGGGAAGAAAGCGAAAGGAGCGGGCGCTAGGGCGC
TGGCAAGTGTAGCGGTCACGCTGCGCGTAACCACCACACCCGCCGCGCTTAATGCGCC
GCTACAGGGCGCGTCCCATTCGCCATTCAGGCTACGCAACTGTTGGGAAGGGCGATCG
GTGCGGGCCTCTTCGCTATTACGCCAGCTGGCGAAGGGGGATGTGCTGCAAGGCGAT
TAAGTTGGGTAACGCCAGGGTTTTCCCAGTCACGACGTTGTAAAACGACGGCCAGTGAA
TTGTAATACGACTCACTATA
```

Figure 10

HCV NS5B (polymerase) sequence [1716 bases]

5'TCTATGTCGTACTCTTGGACCGGCGCCCTGATAACACCGTGTAGTGCT
GAGGAGGAGAAACTGCCCATCAGCCCACTCAGCAACTCCTTGCTGAGAC
ATCATAACCTAGTCTATTCAACGTCGTCTAGAAGCGCTTCTCAGCGTCAG
AGGAAGGTTACCTTCGACAGACTGCAGGTGCTCGACGACCATTACAAGA
CTGTATTAAAGGAGGTAAAGGAGCGAGCGTCTAGGGTAAAGGCTCGCAT
GCTCACCATCGAGGAAGCGTGCGCGCTCGTCCCTCCTCACTCTGCCCGG
TCGAAATTCGGGTATAGTGCGAAGGACGTTCGCTCCTTGTCTAGCAGGG
CCATTAACCAGATCCGCTCCGTCTGGGAGGACTTGCTAGAAGACACCAC
AACTCCAATTCCAACCACCATCATGGCGAAGAACGAGGTGTTTTGTGTGG
ACCCCGCTAAAGGGGGCCGCAAGCCCGCTCGCCTTATCGTGTACCCTGA
CCTGGGGGTTCGTGTCTGCGAGAAACGCGCCCTATATGACGTGATACAG
AAGTTGGCAATTGAGACGATTGGTTCTGCTTACGGATTCCAATACTCGCC
TCAACAGCGGGTCGAACGTCTGCTCAAGATGTGGACCTCAAAGAAAACC
CCCTTGGGGTTCTCGTATGACACCCGCTGCTTTGACTCAACTGTCACTGA
ACAGGACATCAGGGTGGAAGAGGAGATATACCAATGCTGCAACCTTGAA
CCGGAGGCCAGGAAAGTGATCTCCTCCCTCACGGAGCGGCTTTACTGCG
GGGGCCCTATGTTCAACAGCAAGGGGGCTCAGTGTGGTGACCGTCGTTG
CCGTGCCAGTGGAGTTTTGCCTACCAGCTTTGGCAATACAATCACTTGTT
ACATCAAAGCCACAGCGGCTGCGAACGGCGCAGGCCTCCGGGACCCGGA
CTTTCTTGTCTGCGGAGATGATCTGGTCGTGGTGGCCGAGAGTGACGGC
GTCGATGAGGATGGGGCAGCCCTGAGAGCCTTCACGGAGGCTATGACCA
GGTATTCTGCTCCACCCGGAGATGCTCCACAGCCCACCTACGACCTTGA
GCTCATCACATCTTGCTCCTCCAACGTCTCCGTGGCACGGGACGACAAG
GGGAGGAGGTACTATTACCTCACCCGTGATGCCACCACTCCCCTAGCCC
GTGCGGCTTGGGAAACAGCTCGTCACACTCCAGTTAACTCCTGGTTAGG
TAACATCATCATGTACGCGCCTACCATCTGGGTGCGCATGGTAATGATGA
CACACTTTTTCTCCATACTCCAATCCCAGGAGATACTTGATCGACCCCTT
GACTTCGAAATGTACGGGGCCACTTACTCGGTCACGCCGCTGGATTTAC
CAGCAATCATTGAAAGACTCCATGGTCTAAGCGCGTTCACGCTCCACAGT
TACTCTCCAGTAGAGCTCAATAGGGTCGCGGGGACACTCAGGAAGCTGG
GGTGCCCCCCCTACGAGCTTGGAGACATCGGGCACGAGCAGGGCGCGC
TAAGCTTATCGCCCAGGGAGGGAAGGCCAAATATGCGGCCTTTATCTC
TTTAATTGGGCGGTACGCACCAAGACCAAACTCACTCCGCTGCCACGCG
CTGGCCAGTTGGATTTATCCATCTGGTTTACGGTTGGCGTCGGCGGGAA
CGACATTTATCACAGCGTGTCGCGTGCCCGAACCCGCTATTAG 3'

Figure 11

N5266 GCG CGA ATA CGA CTC ACT ATA GAG GGA CAA ACC GCC ATG GCC GAG GTG
AGG CTT CTT GAG TCT GG

N5267 CAT CAT CAT CAT CTT TAT AAT CTG CGG CCG CAC ACT CTC CCC TGT TGA
AGC TCT TGA C

N5268 CCC CTG TTG AAG CTC TTG ACA ATG GGT GAA GTT GAT GTC TTG TGA GTG
GCC TCA CAG

N5269 CTT GTG AGT GGC CTC ACA GGT ATA GCT GTT ATG TCG TTC ATA CTC G

N5343 ACC ATG ATT ACG CCA AGC TCT AAT ACG ACT CAC TAT AGG GAA AGC TCG
CTT GTT C

N5344 AGG GAA AGC TCG CTT GTT CTT TTT GCA GAA GCT CAG AAT AAA CGC TCA
ACT TTG GCC ACC

N5353 TTT ATA ATC TGC GGC CGC CGC CTC GTG TAG AGA CGC AAC

N5354 TTA CTC GCG GCC CAG CCG GCC ATG GCC ATG TCT AAG ACA GCA TCT TCG

N5659 GC AGC TAA TAC GAC TCA CTA TAG GAA CAG ACC ACC ATG GAC GTG GCC
CAG CCT GCT GTG G

N5384 AAA CGC TCA ACT TTG GCC ACC ATG GAT GTG AAG CTT CAG GAG TCT GGG
CC

N5385 GCC CTT GGG CCG GGA GAT GGT CTG CTT CAG TGG CGA GGG CAG GTC
TGT GTG

N5386 CGA GGG CAG GTC TGT GTG GGT CAC GGT GCA CGT GAA CCT CTC CCC
GGA G

N5387 CGT GAA CCT CTC CCC GGA GTT CCA GTC ATC CTC GCA GAT GCT GGC CTC
ACC

N5517 GCG CGA ATA CGA CTC ACT ATA GAG GGA CAA ACC GCC ATG GCC GAT GTG
AAG CTT CAG GAG TCA GG

N5659 GC AGC TAA TAC GAC TCA CTA TAG GAA CAG ACC ACC ATG GAC GTG GCC
CAG CCT GCT GTG G

N5904 TAA TAC GAC TCA CTA TAG GGA AAG GGT TTC TCC GAT CCG GGA ACA TAG
GAT ACC

N5909 TGA GGT ATC CTA TGT TCC GGA TCG GAG AAA CCC ACT CTC CCC TGT
TGA AGC TCT TGA C

N5910 CCG GGA ACA TAG GAT ACC TCA ACC ACC ATG GCC GAG GTG AGG CTT CTT
GAG TCT GG

Figure 14

| Sequence Name | Form of Qβ Replicase | Mutation Found |
|---|---|---|
| A1 | Not included | None |
| A2 | Not included | None |
| A3 | Not included | None |
| A4 | Not included | None |
| A5 | Not included | T149C |
| A6 | Not included | None |
| B1 | Purified | A134G |
| B2 | Purified | A279G |
| B3 | Purified | None |
| B4 | Purified | None |
| B5 | Purified | T89C; G98C; A172C; T244C; A251C |
| B6 | Purified | None |
| C1 | pCDNAQβ | T59C; A129G; A160G |
| C2 | pCDNAQβ | None |
| C3 | pCDNAQβ | A30C; G82A; |
| C4 | pCDNAQβ | None |
| C5 | pCDNAQβ | None |
| C6 | pCDNAQβ | A257G |

Figure 16

Mutation of Replicated RNA by RNA dependent Polymerases: List of Representative Mutations Chosen at Random.

| Coding region; Clone# | Replicase | Mutations |
|---|---|---|
| G1 (anti GlyA 1C3 scFv) | None | None |
| G2 | Qβ purified | G124C, T234C, T329C, G367C, C379T, G385A |
| G3 | Qβ purified | T507G, C527-delete, C543T, C557T |
| G4 | Qβ purified | G136A, insert-141A, -164G, G216A, G330-delete, G429A, C506T, T634C |
| G5 | Qβ purified | C208A, G210C, -211G, C213T, G320A, C403T, C597A |
| G6 | Qβ purified | Deletion 120-441, A440G, G605A, |
| G7 | Qβ purified | A475T, A580C, |
| G8 | Qβ purified | A23C, G23A, G25A, G29A, G109A, G322A, C398T |
| G9 | Qβ purified | G151T, C221-delete, C237T, C249T, |
| HB1 (anti Hepb 4C2 scFv) | None | None |
| HB2 | Qβ purified | G239C, G486T, G354C, |
| HB3 | Qβ purified | A205C, T304G |
| HB4 | Qβ purified | A206C, G274C, T282-delete, T285-delete, G328-delete, G338-C350 substitute irrelevant sequence |
| HB5 | Qβ purified | T397G, G398A, |
| HB6 | Qβ purified | T561C |
| GC1(antiGlyA1C3 scFv) | pCDNAHepC | C57T, G221A, C557T |
| GC2 | HepC purified | Deletion 110-162 |
| GC3 | HepC purified | Deletion 77-165 |
| GC4 | HepC purified | C353A, C366T, | pGE-lysN vector map, source of NS5B (Hepatitis C RNA dependent RNA polymerase) sequence Effect of hepatitis C RdRP expressed in situ on 1C3 scFv RNA template in coupled reaction: RT-PCR

CONTINUOUS IN VITRO EVOLUTION

RELATED APPLICATIONS

This application is the National Phase of PCT/AU99/00341, filed May 7, 1999, designating the U.S. and published as WO 99/58661, with a claim of priority from Australian application no. PP 3445, filed May 8, 1998. All of the foregoing applications, as well as all documents cited in the foregoing applications ("application documents") and all documents cited or referenced in application documents are hereby incorporated herein by reference. Also, all documents cited in this application ("herein cited documents") and all documents cited or referenced in herein cited documents are hereby incorporated herein by reference.

FIELD OF THE INVENTION

The present invention relates to a method for mutating and selecting target binding proteins in a translation system; and to a polynucleotide construct for use in this method. The method of the present invention may be applied to the generation of molecules of diagnostic and therapeutic utility.

BACKGROUND OF THE INVENTION

In vitro evolution of proteins involves introducing mutations into known gene sequences to produce a library of mutant sequences, translating the sequences to produce mutant proteins and then selecting mutant proteins with the desired properties. This process has the potential for generating proteins with improved diagnostic and therapeutic utilities. Unfortunately, however, the potential of this process has been limited by deficiencies in methods currently available for mutation and library generation.

For example, the generation of large libraries (eg beyond a library size of $10^{10}$) of unique individual genes and their encoded proteins has proven difficult with phage display systems due to limitations in transformation efficiency. A further disadvantage is that methods which utilise phage-display systems (FIG. 1) require several sequential steps of mutation, amplification, selection and further mutation (Irving et al., 1996; Krebber et al., 1995; Stemmer. 1994; Winter et al., 1994).

Examples of procedures which have been used to date for affinity maturation of selected proteins, and particularly for the affinity maturation of antibodies, are set out in Table 1. All these methods rely on mutation of genes followed by display and selection of encoded proteins. The particular mutation that is chosen determines the diversity in the resulting gene library. In vitro strategies (Table 1) are severely limited by the efficiency in transformation of mutated genes in forming a phage display library. In one in vivo cyclical procedure (Table 1 No.1), *E. coli* mutator cells there the vehicle for mutation of recombinant antibody genes. The *E. coli* mutator cells MUTD5-FIT (Irving et al., 1996) which bear a mutated DNAQ gene could be used as the source of the S-30 extracts and therefore allow mutations introduced into DNA during replication as a result of proof-reading errors. However, mutation rates are low compared to the required rate. For example, to mutate 20 residues with the complete permutation of 20 amino acid requires a library size of $1 \times 10^{26}$, an extremely difficult task with currently available phage display methodology.

TABLE 1

Affinity maturation strategies

| | Mechanism |
|---|---|
| In vivo | |
| 1 Mutator cells | Random point mutations |
| 2 SIP-SAP | Co-selection and infection with antibody-antigen pairs |
| In vitro | |
| 3 DNA shuffling-sexual PCR | Recursive sequence recombination by DNA homology |
| 4 Site directed mutagenesis over selected regions (CDRs) | Oligonucleotide-coded mutations |
| 5 Chain shuffling | Sequential replacement of heavy or light chain domains using phage libraries |
| 6 Error-prone PCR | Polymerase replication errors |

1) Irving et al. (1996); 2a) Krebber et al. (1995); 2b) Duenas and Borrebaeck (1994); 3) Stemmer (1994), Stemmer et al. (1995); 4) Yang et al. (1995); 5a) Barbas et al. (1994); 5b) Winter et al. (1994); 6) Gram et al (1992).

A selection method which enables the in vitro production of complex libraries of mutants which are continuously evolving (mutating) and from which a desired gene may be selected would therefore provide an improved means of affinity maturation (enhancement) of proteins.

In vitro Coupled Transcription and Translation Systems

It is well known that a DNA plasmid containing a gene of interest can act as template for transcription when controlled by a control element such as the T7 promoter. It is also known that coupled cell-free systems may be used to simultaneously transcribe mRNA and translate the mRNA into peptides (Baranov et al 1993; Kudilicki et al. 1992; Kolosov et al 1992; Morozov et al 1993; Ryabova et al 1989, 1994; Spirin 1990; U.S. Pat. Nos. 5,556,769; 5,643,768; He and Taussig 1997). The source of cell free systems have generally been *E. coli* S-30 extracts (Mattheakis 1994; Zubay 1973) for prokaryotes and rabbit reticulocyte lysates for eukaryotes. Transcription/translation coupled systems have also been reported (U.S. Pat. Nos. 5,492,817; 5,665,563; 5,324,637) involving prokaryotic cell free extracts (Mattheakis et al 1994) and eukaryotic cell free extracts (U.S. Pat. Nos. 5,492,817; 5,665,563) which have different requirements for effective transcription and translation. In addition, there are requirements for the correct folding of the translated proteins in the prokaryotic and eukaryotic systems. For prokaryotes, protein disulphide isomerase (PDI) and chaperones may be required. Generally in prokaryotes translated proteins are folded after release from the ribosome; however, for correct folding of the newly translated protein attached (tethered) to the ribosome a C terminal anchor may also be necessary. An anchor is a polypeptide spacer that links the newly translated protein domain (s) to the ribosome. The anchor may be a complete protein domain such as an immunoglobulin constant region. In complete contrast to this, in eukaryotic systems the protein is folded as it is synthesised and has no requirement for the addition of prokaryote PDI and chaperones. An anchor may however be beneficial in eukaryotic systems for spacing from, and correct folding of, the newly translated protein attached (tethered) to the ribosome.

Polypeptides synthesised de novo in cell-free coupled systems have been displayed on the surface of ribosomes, since for example in the absence of a stop codon the polypeptide is not released from the ribosome. The mRNA ribosome protein complex can be used for selection purposes. This system mimics the process of phage display and selection and is shown in FIG. 1. Features required for optimal display on ribosomes have been described by Hanes and Pluckthun (1997). These features include removal of stop codons. However, removal of stop codons results in the addition of protease sensitive sites to the C terminus of the newly translated protein encoded by a ssrA tRNA-like structure. This can be prevented by the inclusion of antisense ssrA oligonucleotides (Keiler et al 1996).

RNA-directed RNA Polymerases

Qβ bacteriophage is an RNA phage with an efficient replicase (RNA-dependent RNA polymerases are termed replicases or synthetases) for replicating the single-strand genome of coliphage Qβ. Qβ replicase is error-prone and introduces mutations into the RNA calculated in vivo at $10^3$–$10^4$ bases. The fidelity of Qβ replicase is low and strongly biased to replicating its template (Rohde et al 1995). These teachings indicate that replication over a prolonged period leads to accumulation of mutated strands not suitable for synthesis of a desired protein. Both + and − strands serve as templates for replicase; however, for the viral genome the + strand is bound by Qβ replicase and used as the template for the complementary strand (−). In order for RNA replication to occur the replicase requires specific RNA sequence/structural elements which have been well defined (Brown and Gold 1995; Brown and Gold 1996). A reaction containing 0.14 femtograms of recombinant RNA produces 129 nanograms in 30 mins (Lizardi et al 1988).

RNA-directed RNA polymerases are known to replicate RNA exponentially on compatible templates. Compatible templates are RNA molecules with secondary structure such as that seen in MDV-1 RNA (Nishihara, T., et al 1983). In this regard, a vector has been described for constructing amplifiable mRNAs as it possesses the sequences and secondary structure (MDV-1 RNA) required for replication and is replicated in vitro in the same manner as Qβ genomic RNA. The MDV-1RNA sequence (a naturally occurring template for Qβ replicase) is one of a number of natural templates compatible with amplification of RNA by Qβ replicase (U.S. Pat. No. 4,786,600); it possesses RNA-like structures at its terminus which are similar to structures that occur at the ends of most phage RNAs which increase the stability of embedded mRNA sequences. Linearisation of the plasmid allows it to act as a template for the synthesis of further recombinant MDV-1 RNA. (Lizardi et al 1988). Teachings in the art show that prolonged replication by Qβ replicase of a foreign gene require that it be embedded as RNA within one of the naturally occurring templates such as MDV-1RNA.

SUMMARY OF THE INVENTION

The present inventors have now found that RNA directed RNA polymerases introduce mutations into synthesised mRNA molecules during replication in such a manner as to create a library of evolving (mutated) mRNA molecules. These mutated mRNA molecules vary in size due to insertions and deletions as well as point mutations and may be translated in vitro such that the corresponding proteins are displayed, for example, on a ternary complex comprising ribosome, mRNA, and mRNA encoded de novo synthesised protein. The present inventors have also identified conditions in which a large proportion of proteins generated by the ribosome display process are in a correctly folded, functional form. Furthermore, the present inventors have identified conditions in which phage Qβ replicase can function in eukaryotic coupled transcription/translation systems to amplify RNA templates, incorporating mutations into mRNA.

The mRNA molecules in the preferred transcription/ translation system of the present invention are in a continuous cyclic process of replication/mutation/translation leading to a continuous in vitro evolution (CIVE) process.

This CIVE process provides a novel method for in vitro evolution of proteins which avoids the limitation of numbers, library size and the time consuming steps inherent in previous affinity maturation processes.

Accordingly, in a first aspect the present invention provides a method for the mutation, synthesis and selection of a protein which binds to a target molecule, the method comprising:

(a) incubating a replicable mRNA molecule encoding the protein with ribonucleoside triphosphate precursors of RNA and an RNA-directed RNA polymerase, wherein the RNA-directed RNA polymerase replicates the mRNA molecule but introduces mutations thereby generating a population of mutant mRNA molecules;

(b) incubating the mutant mRNA molecules from step (a) with a translation system under conditions which result in the synthesis of a population of mutant proteins such that after translation, mutant proteins are linked to their encoding mRNA molecules thereby forming a population of mutant protein/mRNA complexes;

(c) selecting one or more mutant protein/mRNA complex(es) by exposing the population of mutant protein/ mRNA complexes from step (b) to the target molecule and recovering the mutant protein/mRNA complex(es) bound thereto; and (d) optionally releasing the mRNA molecules from the complex(es).

In a second aspect the present invention provides a method for the mutation, synthesis and selection of a protein which binds to a target molecule which includes:

(b) incubating the mutant mRNA molecules from step (a) with a translation system under conditions which result in the synthesis of a population of mutant proteins such that after translation, mutant proteins are linked to their encoding mRNA molecules thereby forming a population of mutant protein/mRNA complexes;

(c) selecting one or more mutant protein/mRNA complex(es) by exposing the population of mutant protein/ mRNA complexes from step (b) to the target molecule;

(d) repeating steps (a) to (c) one or more times, wherein the replicable mRNA molecule used in step (a) is the mRNA obtained from complex(es) selected in step (c);

(e) recovering mutant protein complexes bound to the target molecule(s); and (f) optionally releasing or recovering the mRNA molecules from the complex(es).

The mRNA from step (d) may be recycled through steps (a) to (c) without purification or isolation from the translation system.

In one embodiment, the mRNA from step (d) is recycled via step (a) while the mRNA is attached to the complex(es) obtained in step (c). In another embodiment, the mRNA is released from the complex(es) obtained in step (c) prior to recycling. The mRNA may be released from the complexes by any suitable mechanism. The mechanism may include raising the temperature of the incubation, or changing the concentration of the compounds used to maintain the complexes intact.

In the context of the present invention, the mRNA may be recycled through steps (a) to (c) by sequential, manual steps. In a preferred embodiment, however, steps (a), (b), (c) and (d) are carried out simultaneously in a single or multiple chambered reaction vessel and the recycling occurs automatically within the vessel.

In the context of the present invention, the mRNA may be recycled through steps (a) to (c) by sequential, manual steps. In a preferred embodiment, however, steps (a), (b), (c) and (d) are carried out simultaneously in a single reaction vessel and the recycling occurs automatically within the vessel.

In another embodiment of the second aspect, the mRNA from step (d) is isolated. The isolated mRNA may be transcribed into cDNA. The resulting cDNA may be cloned into a vector suitable for expression of the encoded protein.

It will be appreciated by those skilled in the art that any suitable complex may be used to link the translated proteins to their encoding mRNAs. For example, the complex may be a mitochondria or other cell organelle suitable for protein display. In a preferred embodiment, the complex is an intact ternary ribosome complex. The ribosome complex preferably comprises at least one ribosome, at least one mRNA molecule and at least one translated polypeptide. This complex allows "ribosome display" of the translated protein. Conditions which are suitable for maintaining ternary ribosome complexes intact following translation are known. For example, deletion or omission of the translation stop codon from the 3' end of the coding sequence results in the maintenance of an intact ternary ribosome complex. Sparsomycin or similar compounds may be added to prevent dissociation of the ribosome complex. Maintaining specific concentrations of magnesium salts and lowering GTP levels may also contribute to maintenance of the intact ribosome complex.

It will be appreciated by those skilled in the art that preferred embodiments of the present invention involve coupled replication-translation-selection in a recycling batch process, and preferably, in a continuous-flow process (see, for example, FIG. 4). Continuous-flow equipment and procedures for translation or transcription-translation are known in the art and can be adapted to the methods of this invention by changing the composition of materials or conditions such as temperature in the reactor. Several systems and their methods of operation are reviewed in Spirin, A. S. (1991), which is incorporated by reference herein. Additional pertinent publications include Spirin et al. (1988); Rattat et al. (1990); Baranov et al. (1989); Ryabova et al. (1989); and Kigawa et al. (1991), all of which are incorporated by reference herein.

By "translation system" we mean a mixture comprising ribosomes, soluble enzymes, transfer RNAs, and an energy regenerating system capable of synthesizing proteins encoded by exogenous mRNA molecules.

In a preferred embodiment, the translation system is a cell-free translation system. Translation according to this embodiment is not limited to any particular cell-free translation system. The system may be derived from a eukaryote, prokaryote or a combination thereof. A crude extract, a partially purified extract or a highly purified extract may be used. Synthetic components may be substituted for natural components. Numerous alternatives are available and are described in the literature. See, for example, Spirin (1990b), which is incorporated by reference herein. Cell free translation systems are also available commercially. In one embodiment of the present invention the cell-free translation system utilises an S-30 extract from *Escherichia coli*. In another embodiment, the cell-free translation system utilises a reticulocyte lysate, preferably a rabbit reticulocyte lysate.

The translation system may also comprise compounds which enhance protein folding. To this end, the present inventors have identified conditions in which an increased proportion of proteins produced by the ribosome display process are generated in a folded, functional form. These conditions include the addition of reduced and/or oxidised glutathione to the translation system at a concentration of between 0.1 mM and 10 mM. Preferably, the translation system comprises oxidised glutathione at a concentration of between 2 mM to 5 mM. Preferably, the translation system comprises oxidised glutathione at a concentration of about 2 mM and reduced gluthatione at a concentration of between 0.5 mM and 5 mM.

In another embodiment of the present invention the translation system consists of or comprises a cell or compartment within a cell. The cell may be derived from a eukaryote or prokaryote.

A number of RNA-directed RNA polymerases (otherwise known as replicases or RNA synthetases) known in the art have been isolated and are suitable for use in the method of the present invention. Examples of these include bacteriophage RNA polymerases, plant virus RNA polymerases and animal virus RNA polymerases. In a preferred embodiment of the present invention, the RNA-directed RNA polymerase introduces mutations into the replicated RNA molecule at a relatively high frequency, preferably at a frequency of at least one mutation in 10 bases, more preferably one mutation in $10^3$ bases. In a more preferred embodiment the RNA-directed RNA polymerase is selected from the group consisting of Qβ replicase, Hepatitis C RdRp. Vesicular Stomatitis Virus RdRp, Turnip yellow mosaic virus replicase (Deiman et al (1997) and RNA bacteriophage phi 6 RNA-dependent RNA (Ojala and Bamford (1995). Most preferably, the RNA-directed RNA polymerase is Qβ replicase.

The RNA-directed RNA polymerase may be included in the transcription/translation system as a purified protein. Alternatively, the RNA-directed RNA polymerase may be included in the form of a gene template which is expressed simultaneously with step (a), or simultaneously with steps (a), (b) and (c) of the methods of the first or second aspects of the present invention.

In a further preferred embodiment, the RNA-directed RNA polymerase may be fused with or associated with the target molecule. Without wishing to be bound by theory, it is envisaged that in some cases, the binding affinity of the translated protein may be greater than the affinity of the replicase for the mRNA molecule. The binding of the mutant protein/mRNA complex to a target molecule/RNA-directed RNA polymerase fusion construct would bring the mRNA into the proximity of the RNA-directed RNA polymerase. This may result in preferential further replication and mutation of mRNA molecules of interest.

RNA templates that are replicated by various RNA-dependent RNA polymerases are known in the art and may serve as vectors for producing replicable mRNAs suitable for use in the present invention. Known templates for Qβ replicase include RQ135 RNA, MDV-1 RNA, microvariant RNA, nanovariant RNAs, CT-RNA and RQ120 RNA. Qβ RNA, which is also replicated by Qβ replicase, is not preferred, because it has cistrons, and further because the products of those cistrons regulate protein synthesis. Preferred vectors include MDV-1 RNA and RQ135 RNA. The sequences of both are published. See Kramer et al. (1978) (MDV-1 RNA) and Munishkin et al. (1991) J (RQ135), both of which are incorporated by reference herein. They may be made in DNA form by well-known DNA synthesis techniques.

In a preferred embodiment of the first aspect of the present invention, the method further includes the step of transcribing a DNA construct to produce replicable mRNA. DNA encoding the recombinant mRNA can be, but need not be, in the form of a plasmid. It is preferable to use a plasmid and an endonuclease that cleaves the plasmid at or near the end of the sequence that encodes the replicable RNA in which the gene sequence is embedded. Linearization can be performed separately or can be coupled with transcription-replication-translation. Preferably, however, linear DNA is generated by any one of the many available DNA replication reactions and most preferably by the technique of Polymerase Chain Reaction (PCR). For some systems non-linearized plasmids without endonuclease may be preferred. Suitable plasmids may be prepared, for example, by following the teachings of Melton et al (1984a,b) regarding processes for generating RNA by transcription in vitro of recombinant plasmids by bacteriophage RNA polymerases, such as T7 RNA polymerase or SP6 RNA polymerase. See, for example, Melton et al. (1984a) and Melton (1984b), which are incorporated by reference herein. It is preferred that transcription begin with the first nucleotide of the sequence encoding the replicable RNA.

In a further preferred embodiment the transcription is carried out simultaneously in a single or multiple chambered reaction vessel, or reactor, with steps (a), (b), (c) of the method according to the first or second aspects of the present invention.

The target molecule may be any compound of interest (or a portion thereof) such as a DNA molecule, a protein, a receptor, a cell surface molecule, a metabolite. an antibody, a hormone a bacterium or a virus.

In a preferred embodiment, the target molecule is bound to a matrix and added to the reaction mixture comprising the complex (displaying translated proteins). The target molecule may be coated, for example, on a matrix such as magnetic beads. The magnetic beads may be Dynabeads. It will be appreciated that the translated proteins will competitively bind to the target molecule. Proteins with higher affinity will preferably displace lower affinity molecules. Thus, the method of the present invention allows selection of mutant proteins which exhibit improved binding affinities for a target molecule of interest.

The present inventors have also made the surprising findings that minimal sequences derived from naturally occurring replicase templates, such as the MDV-1 template, are sufficient for the binding of Qβ replicase. On the basis of this finding a novel construct suitable for transcription of replicable mRNA has been developed.

Accordingly, in a preferred embodiment of the first or second aspects of the present invention, the method further includes transcribing a DNA construct to produce a replicable mRNA molecule, wherein the DNA construct comprises:

(i) an untranslated region comprising a control element which promotes transcription of the DNA into mRNA and a ribosome binding site;

(ii) an open reading frame encoding the protein which binds to the target molecule; and (iii) a stem-loop structure situated upstream of the open reading frame.

In a third aspect the present invention provides a DNA construct comprising:

(i) an untranslated region comprising a control element which promotes transcription of the DNA into mRNA and a ribosome binding site;

(ii) a cloning site located downstream of the untranslated region; and (iii) a replicase binding sequence located upstream of the cloning site.

When used herein the phrase "replicase binding sequence" refers to a polynucleotide sequence which as a "loop-like" secondary structure which is recognised by a replicase (in particular, a replicase holoenzyme). Preferably, the replicase binding sequence does not include a full length RNA template for a replicase molecule. For example, preferably the phrase "replicase binding sequence" does not include full length MDV-1 RNA or RQ135 RNA templates.

In a preferred embodiment, the replicase binding sequence is between 15 to 50 nucleotides in length, more preferably between 20 and 40 nucleotides in length. Preferably, the replicase binding sequence is recognised by Qβ replicase.

In a further preferred embodiment, the sequence of the replicase binding sequence comprises or consists of the sequence:
GGGACACGAAAGCCCCAGGAACCUUUCG (SEQ ID NO: 27).

In a further preferred embodiment, a second replicase binding sequence is included downstream of the cloning site.

Any suitable ribosome binding site may be used in the construct of the present invention. Prokaryotic and eukaryotic ribosome binding sequences may be incorporated depending on whether prokaryotic or eukaryotic systems are being used. A preferred prokaryotic ribosome binding site is that of the MS2 virus.

In a further preferred embodiment, the DNA construct includes a translation initiation sequence. Preferably, the translation initiation sequence is ATG.

It will be apparent to those skilled in the art that any gene of interest may be inserted into the cloning site in the DNA construct. In a preferred embodiment the gene(s) of interest is a nucleotide sequence coding for (i) a library of target binding proteins or (ii) a single target binding protein, where the target could include any of protein, DNA, cell surface molecules, receptors, antibodies, hormones, viruses or other molecules or complexes or derivatives thereof.

A nucleotide sequence coding for an anchor domain may be fused 3' in frame with the gene of interest. The anchor domain may be any polypeptide sequence which is long enough to space the protein translated from the gene of interest a sufficient distance from the ribosome to allow correct folding of the molecule and accessibility to its cognate binding partner. Preferably, the polypeptide has a corresponding RNA secondary structure which mimics that of a replicase template. In a preferred embodiment, the polypeptide is an immunoglobulin constant domain. Preferably, the polypeptide is a constant light domain. The constant light domain may be the first constant light region of the mouse antibody 1C3. Preferably, the constant domain is encoded by the sequence shown in FIG. 5a. Alternatively, the polypeptide may be the human IgM constant domain. In another embodiment the anchor may be selected from the group consisting of: the octapeptide "FLAG" epitope. DYKDDDDK (SEQ ID NO: 29) or a polyhistidine$_6$ tag followed optionally by a translation termination (stop) nucleotide sequence. The translation termination (stop) nucleotide sequence may be TAA or TAG. In some constructs of the present invention, no stop codons are present so as to prevent recognition by release factors and subsequent protein release. In these constructs, the anti-sense ssrA oligonucleotide sequence may be added to prevent addition of a C terminal protease site in the 3' untranslated region that follows.

In a fourth aspect the present invention provides a kit for generating a replicable mRNA transcript which includes a DNA construct according to the second aspect of the present invention.

In a preferred embodiment the kit includes at least one other additional component selected from
(i) an RNA-directed RNA polymerase, preferably Qβ replicase, or a DNA or RNA template for an RNA-directed RNA polymerase;
(ii) a cell free translation system;
(iii) a DNA directed RNA polymerase, preferably a bacteriophage polymerase;
(iv) ribonucleoside triphosphates; and
(v) restriction enzymes.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

BRIEF DESCRIPTION OF THE FIGURES

FIGS. 5(a), (b), (c) and (d): Nucleotide sequences of: a) the first constant light region of mouse monoclonal antibody 1C3 (SEQ ID NO: 1); b) the third constant heavy region of the human IgM antibody (SEQ ID NO: 2); c) the anti glycophorin (1C3) scFv (SEQ ID NO: 3); d) the anti-HepatitisB surface antigen (4C2) scFv (SEQ ID NO: 4).

FIGS. 6(a), (b), (c) and (d): DNA sequence of the plasmid pBRT7Qbeta containing a cDNA copy of the Qβ bacteriophage genome (SEQ ID NO: 5).

FIG. 10: DNA sequence of the Hepatitis C virus RNA dependent RNA polymerase (SEQ ID NO: 6).

FIG. 11: DNA sequences of oligonucleotides used as primers in PCR reactions to generate template DNA for in vitro coupled transcription/translation reactions. Nucleotide sequences of oligonucleotides used for both the generation of templates and the recovery of products after panning. Sequences are numbered and are written 5' to 3' (SEQ ID NO: 7–24).

FIG. 14: Effect of including Qβ replicase in coupled transcription and translation; Table of mutations in the sequences of selected mutants. This figure shows the positions and type of mutations found in 280 nucleotides of sequence from 6 random clones. These had been recovered from pannings of the anti-GlyA scFv against GlyA coated Dynabeads after transcription and translation either in the absence of Qβ replicase, in the presence of purified Qβ or in the presence of plasmid pCDNAQβ. In the "Mutation Found" column; "None" means that no mutations were found; Mutations are shown in the form AxB where A is the wild type nucleotide, x is the position number within the sequence (as presented in FIG. 5c) and B is the mutated nucleotide observed.

FIG. 16: DNA sequence analysis of replication and mutation of anti glycophorin scFv and anti Hepatitis B scFv by Qβ replicase from T7 polymerase transcripts.

DETAILED DESCRIPTION OF PREFERRED EMBODIMENTS OF THE INVENTION

In a preferred aspect of the present invention, the system for continuous one-step evolution of proteins comprises the following components:

The Expression Unit

Figure 1:
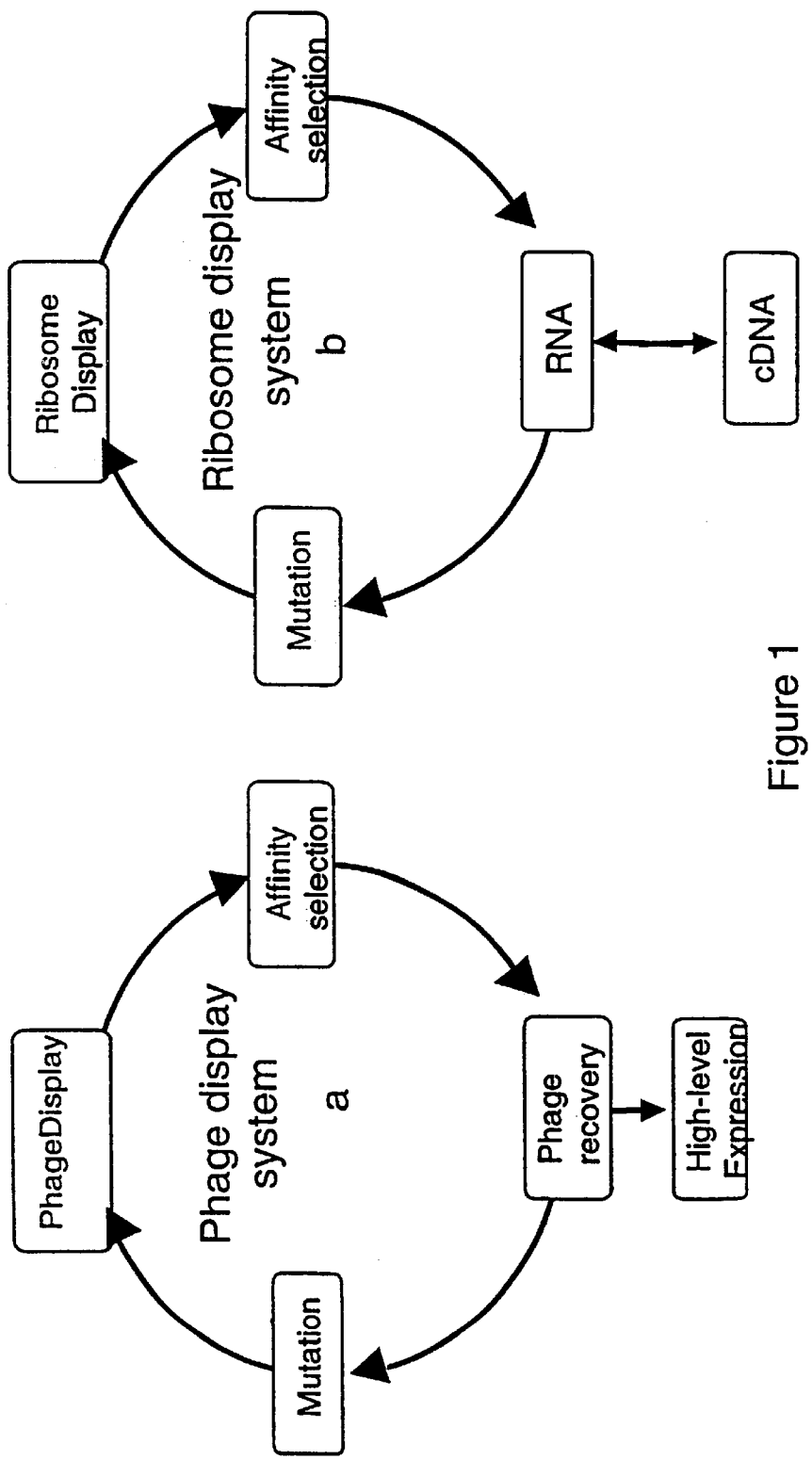
FIG. 1: Affinity maturation cycle for a) phage display and b) ribosome display in the continuos in-vitro evolution (CIVE) process.
Figure 2:
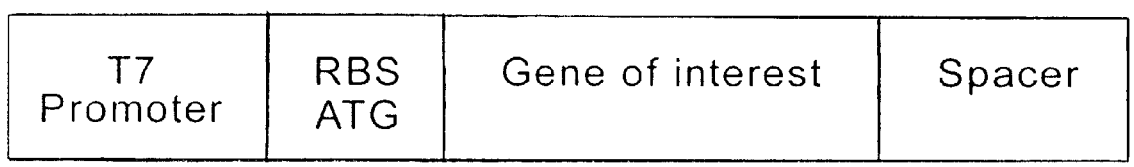
FIG. 2: Schematic representation of an expression unit containing a gene of interest (nucleotide sequence) for CIVE. The expression unit comprises a gene of interest with upstream ribosome binding site (RBS) and translational initiation site (ATG) along with a transcriptional initiation sequence (T7 promoter). The construct also comprises a downstream spacer sequence.

A preferred expression unit for use in the present invention is depicted in FIG. 2. This expression unit comprises 3' and 5' untranslated regions with in the 5' untranslated region a control element such as the T7 or SP6 promoter to promote transcription of the DNA into mRNA. The consensus DNA sequences are specific for their polymerases; the T7 promoter sequence for T7 RNA polymerase is: TAATACGACT-CACTATAGGGAGA (SEQ ID NO: 28). The T7 promoter sequence may act as an RNA dependent RNA polymerase binding sequence (ie. it may act as a binding sequence for Qβ replicase). Preferably, however, the construct includes a stemloop structure for the binding of Qβ replicase, located in the 5' untranslated region 3' to the promoter site. Preferably, a second stemloop structure is included downstream of the coding sequence, preferably about 1 kb 3' of translation termination site of the expression unit. The preferred sequence of the stemloop structure is: GGGA-CACGAAAGCCCCAGGAACCUUUCG (SEQ ID NO: 27).

The ribosome binding site is the next region downstream of the promoter. Any of several ribosome binding be used in this position. Prokaryotic and eukaryotic ribosome binding sequences may be incorporated depending on whether a eukaryotic or prokaryotic coupled system is being used. One preferred prokaryotic binding site is that of the MS2 virus. The translation initiation sequence ATG is preferably used and codes for the amino acid methionine; this is the start of in vitro translation.

The Gene (Nucleotide Sequence) of Interest

It will be apparent to those skilled in the art that the gene of interest can be attached to the untranslated regions by any of the standard genetic techniques. The gene of interest may include any nucleotide sequence with an open reading frame (no stop codons) up to the 3' end of the gene and for the purposes of this invention the end of the anchor (spacing) sequence.

In a preferred embodiment the gene(s) of interest is a nucleotide sequence coding for i) a library of target binding proteins or ii) a single target binding protein, where the target may include any of protein, DNA, cell surface molecules. receptors, antibodies, hormones, viruses or other molecules or complexes or derivatives thereof. A nucleotide sequence coding for an anchor domain may be fused 3' and in frame with the gene of interest. The anchor domain may be any of a series of polypeptide sequences sufficiently long to space the protein translated from the gene of interest a sufficient distance from the ribosome to allow correct folding of the molecule and accessibility to its cognate binding partner. In a preferred embodiment the anchor is the sequence coding for the octapeptide "FLAG" epitope: DYKDDDDK (SEQ ID NO: 29) or any of the human or murine antibody constant domains. Preferably, the anchor is the constant domain from a mouse monoclonal antibody, such as constant domain 1C3 (see FIG. 5a). A further preferred anchor is the constant region from a human IgM antibody (see FIG. 5b).

The anchor sequence may be followed by a translation termination (stop) nucleotide sequence e.g. TAA or TAG. However, in some constructions it could be envisaged that no stop codons should be present to prevent recognition by release factors and subsequent protein release. In these, the anti-sense ssrA oligonucleotide sequence is added to prevent addition of a C terminal protease site in the 3' untranslated region that follows. The addition of sparsomycin, other similar compounds or a reduction in temperature also prevents release of the ribosome from the mRNA and de novo synthesised protein.

The Expression System

Transcription/replication/mutation for the expression unit may be achieved by use of a rabbit reticulocyte lysate system (He and Taussig, 1997) or an E. coli S-30 transcription translation mix (Mattheakis et al., 1994; Zubay, 1973). For example a DNA expression unit (detailed above) with a T7 promoter is treated with T7 RNA polymerase according to the manufacturers instructions. The resulting RNA library reflects the diversity of the encoded genes. RNA dependent-RNA polymerases added for replication and mutation can be supplied either as purified enzyme or alternatively encoded as a distinct expression unit in a plasmid under control of a promoter such as T7 or SP6. The preferred enzyme is Qβ replicase although any enzyme with similar characteristics may be used. This step provides the increase in complexity of the library through mutation by the Qβ replicase. For mRNA synthesis in eukaryotic cells the mRNA is preferably capped which is achieved by adding an excess of diguanosine triphosphate; however, the rabbit reticulocyte system from the commercial suppliers Promega and Novagen have components in the system to make the addition of capping compounds unnecessary. The transcription/translation mix or coupled system may be extracted from any cell, those most commonly used are wheat germ, mammalian cells such as HeLa cells E. coli and rabbit reticulocytes. The coupled transcription translation system may be extracted from the E. coli mutator cells MUTD5-FIT (Irving et al., 1996) which bear a mutated DNAQ gene and therefore allow further random mutations introduced into DNA during replication as a result of proofreading errors. One preferred transcription/translation mix is the rabbit reticulocyte lysate. Addition of GSSG to the coupled system enhances correct folding of displayed proteins and therefore enhances subsequent binding and selection to counter-receptors or antigens.

Mutation by Qβ Replicase

Figure 3:
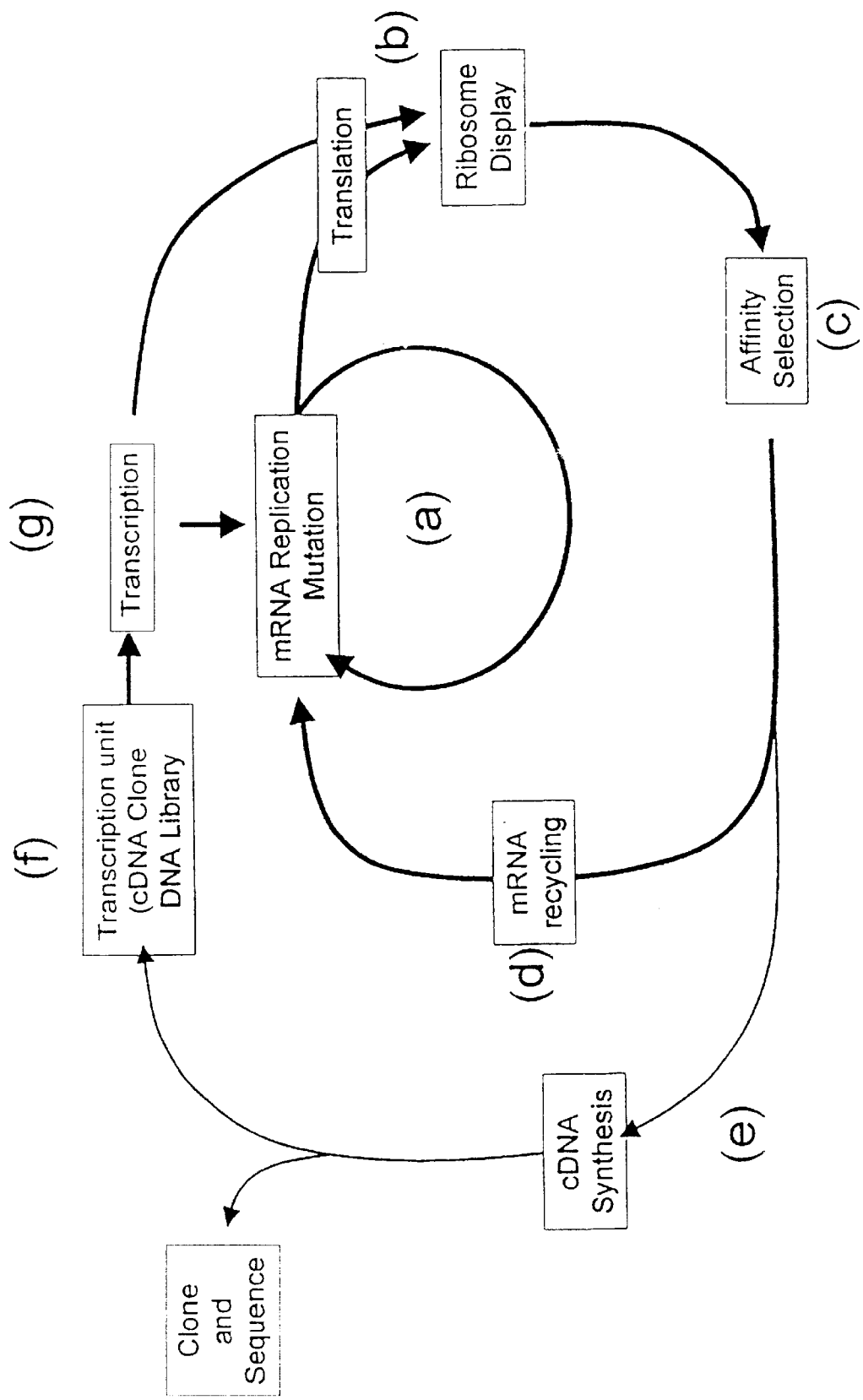
FIG. 3: Schematic representation of the CIVE method showing the continuous cycling nature of in vitro affinity maturation. The method enables the in vitro production of complex libraries of mutants which are continuously evolving (mutating) and from which a desired gene may be selected; the mRNA molecules in the preferred transcription/translation system of the present invention are in a continuous cyclic process of replication/mutation/translation leading to continuous in vitro evolution (CIVE).

The Qβ replicase is included in the system for the replication and production of high levels of mRNA incorporating random mutations (see FIG. 3). Multiple copies of a single-stranded RNA template is replicated with mutations by the Qβ replicase into its single stranded complement; however, both strands are equally efficient as template under isothermal conditions.

Teaching in the art indicates that the complex and stable secondary and tertiary structures present in full length RNA from phages such as Qβ limit the access of ribosomes to the protein initiation sites. However, we have found that smaller RNA sequences are suitable for binding of replicases and therefore may be used instead of full length templates. Preferred sequences are small synthetic RNA sequences known as pseudoknots (Brown and Gold 1995;1996) which are compatible with amplification by Qβ replicase. In the context of the present invention, the use of pseudoknots can overcome the problems of ribosome access to the protein initiation sites whilst maintaining the binding sites necessary and sufficient for the Qβ replicase amplification of the RNA and sequences fused thereto.

Translation and Ribosome Display

Several in vitro translation methods are known which may be either eukaryotic such as rabbit reticulocyte lysate and wheatgerm, or prokaryotic such as E. coli. These are available commercially or can be generated by well known published methods. Translation of the mutated mRNAs produces a library of protein molecules, preferably attached to the ribosome in a ternary ribosome complex which includes the encoding specific mRNA for the de novo synthesised protein (Mattheakis et al., 1994). Several methods are known to prevent dissociation of the mRNA from the protein and ribosome. For example, sparsomycin or similar compounds may be added; sparsomycin inhibits peptidyl transferase in all organisms studied and may act by formation of an inert complex with the ribosome (Ghee et al., 1996). Maintaining high concentrations of magnesium salts and lowering GTP levels may also contribute to maintaining the ribosome/mRNA/protein complex; in conjunction with the structure of the expression unit detailed above. A preferred means to maintain the ternary ribosome complex is the omission of the translation stop codon at end of the coding sequence.

In addition, there are preferred requirements for the correct folding of the molecules in the two systems. For prokaryotes protein disulphide isomerase (PDI) and chaperones may be used as well as a C terminal anchor domain to ensure the correct folding. The latter is required as prokaryotic proteins are released from the ribosome prior to folding (Ryabova et al., 1997) and therefore in situations in which the peptide is anchored to the ribosome the entire protein needs to be spaced from the ribosome. In contrast to this in eukaryotic systems the protein is folded as it is synthesised and has no requirement for the prokaryote PDI and chaperones to be added; however, we have found that addition of a specific range of GSSG concentrations is beneficial to the library selection by the enhanced display of correctly folded proteins on the ternary ribosome complexes.

Selection and Competitive Binding

Successive rounds of RNA replication produce libraries of RNA molecules which on translation produce libraries of proteins. A target molecule-bound matrix (for example antigen-coated Dynabeads) may be added to the reaction to capture ternary ribosome complexes. The individual members in the library compete for the antigen immobilised on the matrix (Dynabeads). Molecules with a higher affinity will displace lower affinity molecules. At the completion of the process the complexes [mRNA/ribosomes/protein] attached to matrix (Dynabeads) may be recovered, cDNA may be synthesised from the mRNA in the complex and cloned into a vector suitable for high-level expression from the encoded gene sequence.

Figure 4:
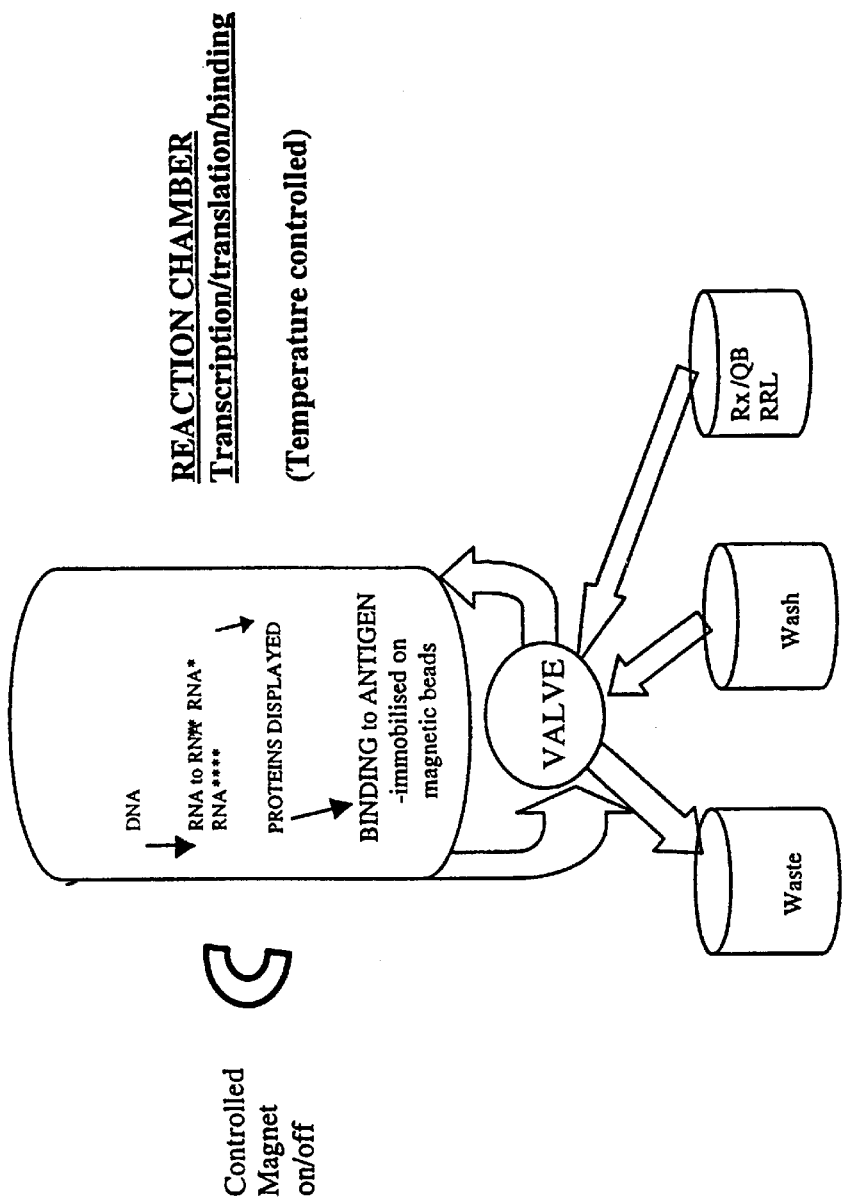
FIG. 4: Representation of a reaction vessel suitable for the CIVE process.

A recycling flow system (Spirin et al., 1988) may be applied to this Continuous in vitro Evolution (CIVE) system using a thermostated chamber to ensure supply of substrates (including ribosomes) and reagents and removal of non-essential products. All processes of CIVE may take place within this chamber including: coupled transcription and translation, mutating replication, display of the de novo synthesised protein on the surface of the ternary ribosome complex and competitive binding of the displayed proteins on the ternary ribosome complex to antigen to select those with the highest affinity binding (FIG. 4). The unbound reagents, products and displayed proteins are removed by flushing with washing buffer and the bound ternary ribosome complexes are dissociated by increasing the temperature and omitting the magnesium from the buffer. This is followed with the addition of all the reagents necessary to carry out all the above steps except the washing buffer steps. Methods are available to prevent dissociation of the mRNA from the protein and ribosome such as the addition of sparsomycin or similar compounds, maintaining specific concentrations of magnesium salts and lowering GTP levels may also contribute to maintaining the ribosome/mRNA/protein complex as well as reducing the reaction temperature or omitting translational stop codons. By using vessels whose temperatures are controlled combined with a continuous flow capability, mRNAs from selected ribosomes may be dissociated from the ribosomes and further replicated, mutated and translated as the concentration of reagents important for the maintenance of the ribosome/mRNA/protein complex such as sparsomycin. Mg etc are varied. FIG. 4 depicts the design of a such a device.

The present invention will now be more fully described with reference to the following non-limiting Examples.

EXAMPLE 1

Recombinant Qβ Replicase: Expression and Purification

Cloning and Expression

The Qβ replicase coding sequence was amplified by PCR from the plasmid pBRT7Qβ, a pBR322 based construction (briefly described in Barrera et al., 1993) that was designed to allow the preparation of infectious RNA by transcription using T7 RNA polymerase in vitro; being a cDNA copy of the RNA genome of phage Qβ. The sequence of pBRT7Qβ is shown in FIG. 6. Nucleotide no. 1 is the first nucleotide of the Qβ replicase sense strand. The oligonucleotides used as primers to amplify the Qβ replicase encoded sites for restriction enzyme digestion by the enzymes FcoRI and Not I and the sequences are shown in FIG. 11.

Figure 7A:
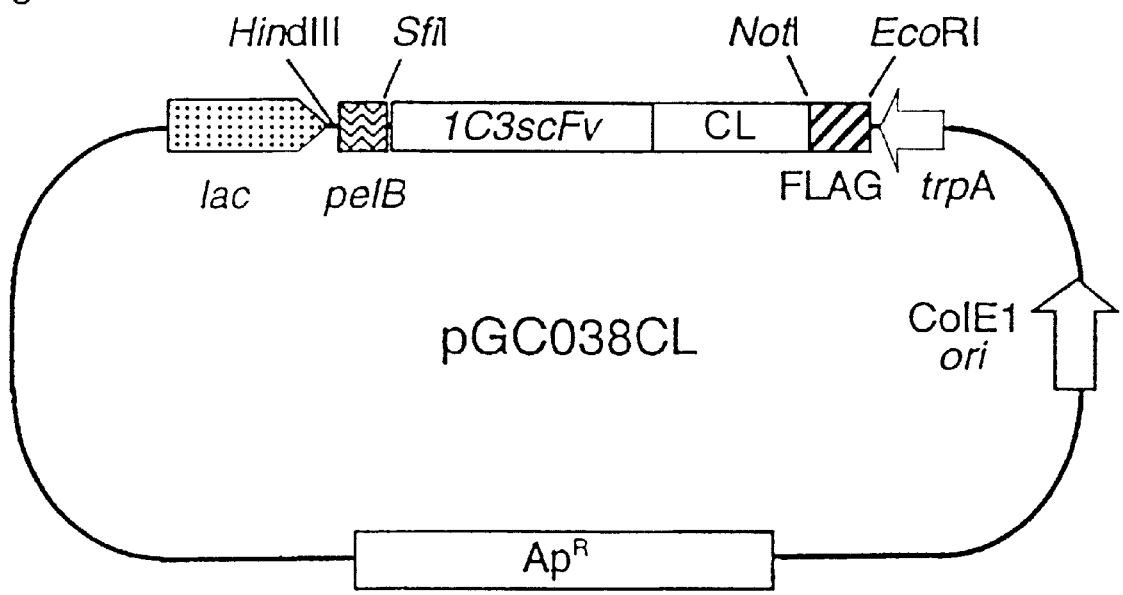
FIGS. 7(a) and (b): Schematic representation of the plasmids (a) pGC038CL (containing the anti-glycophorin scFv (1C3) and the mouse constant light region) and (b) pGC_CH (containing the human constant heavy region), which were used for the PCR synthesis of template used for in vitro transcription and translation. These plasmids were used to supply downstream spacer sequences. In most cases, genes of interest were cloned into SfiI and NotI sites of pGC_CH.

The PCR products were purified using any one of the commercial products available for this purpose (for example Bresatec). The purified DNA was cloned into the EcoRI and NotI sites of the vector pGC (FIG. 7a) using standard molecular biology techniques. The vector pGC and expression of recombinant protein therefrom has been described in the literature and is incorporated herein by reference (Coia et al., 1996). The process of the PCR amplification and cloning of the Qβ replicase gene into vectors and transformation into E. coli for expression of the enzyme will be known to those skilled in the art as will be the expression of the Qβ replicase gene in pGC which was induced by adding 1 mM ispropylthiogalatoside (IPTG) to the culture medium.

Expression and purification of the Qβ replicase gene in the pBR322 based vector with the promoter PL was performed as detailed below. The rep14 Billeter strain was supplied by Christof Biebricher, Max Planck, Gottingen. The E. coli strain was grown in a 20 l fermentor in 2% nutrient broth, 1.5% yeast extract. 0.5% NaCl, 0.4% glycerol, 100mg/l ampicillin with good aeration at 30° C. to an optical density of 2 (660 nM). After raising the temperature to 37° C., aeration was continued for 5 h. The cells were chilled on ice and harvested by centrifugation (yielding about 180 g wet cell mass).

Purification of Qβ Replicase

Buffer A: 0.05M Tris.HCl-buffer (pH 7.8), 1 mM mercaptoethanol, 20% v/v glycerol, 100 mg/l ampicillin.
Buffer B: 0.05M HEPES.Na-buffer (pH 7.0), 1 mM mercaptoethanol, 20% v/v glycerol.

50 g harvested E. coli were homogenized with 100 ml. 0.05M Tris.HCl buffer (pH 8.7) 1 mM mercaptoethanol in a high-speed blender. Lysozyme and EDTA were added to final concentrations of 100 µg/ml and 0.5 mM, respectively, and the solution was gently stirred at 0° C. for 30 min. 12 ml 8% Na deoxycholate, 0.24 ml phenylsulfonylfluoride (20 mg/ml in propanol-2), 0.15 ml Bacitracine (10 mg/ml), 0.15 ml 0.1M benzamidine, 3.3 ml 10% Triton-X-100 were added and the solution adjusted with $MgCl_2$ to 10 mM final concentration. The high viscosity was reduced by blending at high speed. Solid NaCl was added to a final concentration of 0.5M and 4.8 ml 0.3% polyethyleneimine (pH 8) was added with stirring. After stirring for 20 min at 0° C. the suspension was centrifuged for 30 min at 10,000 rpm (GSA rotor). After dilution of the supernatant with 5 volumes Tris.HCl buffer (pH 8.7) 1 mM mercaptoethanol, 100 ml DEAE cellulose slurry (Whatman DE52. equilibrated with buffer A) was added and slowly stirred at 0° C. for 20 min. After 40 min incubation without stirring, the supernatant was decanted from the sediment and discarded. The sediment was suspended in buffer A, poured into a glass column of 1 cm diameter, washed with 400 ml Tris.HCl buffer (pH 8.7) 1 mM mercaptoethanol, and eluted with 250 ml buffer A+180 mM NaCl; fractions were collected. The fractions were assayed for the presence of Qβ replicase using the following binding assay.

Enzyme Location Assay: Binding of Biotinylated RNA to Qβ Replicase

This is a non-radioactive assay developed to detect replication enzymes which relies on biotin-labelled RNA bound to enzyme being retained on positively charged membranes; whereas, free biotin-labelled RNA under the same conditions is not retained on the membrane. DNA and RNA were labelled with psoralen-biotin (Ambion) according to the manufacturers instructions. The labelled RNA was then added to the column eluate (sample fractions) as indicated in the assay below to detect the location of Qβ replicase. The following was mixed in an Eppendorf tube:

10 µl column eluate fractions

10 µl 0.5M Tris HCl (pH 7.4) containing 120 mM MgCl$_2$

10 µl 2 mM ATP

10 µl 5 mM ATP

10 µl~100 ng/ml psoralen-biotin labelled probe RNA

50 µl water

Figure 12:
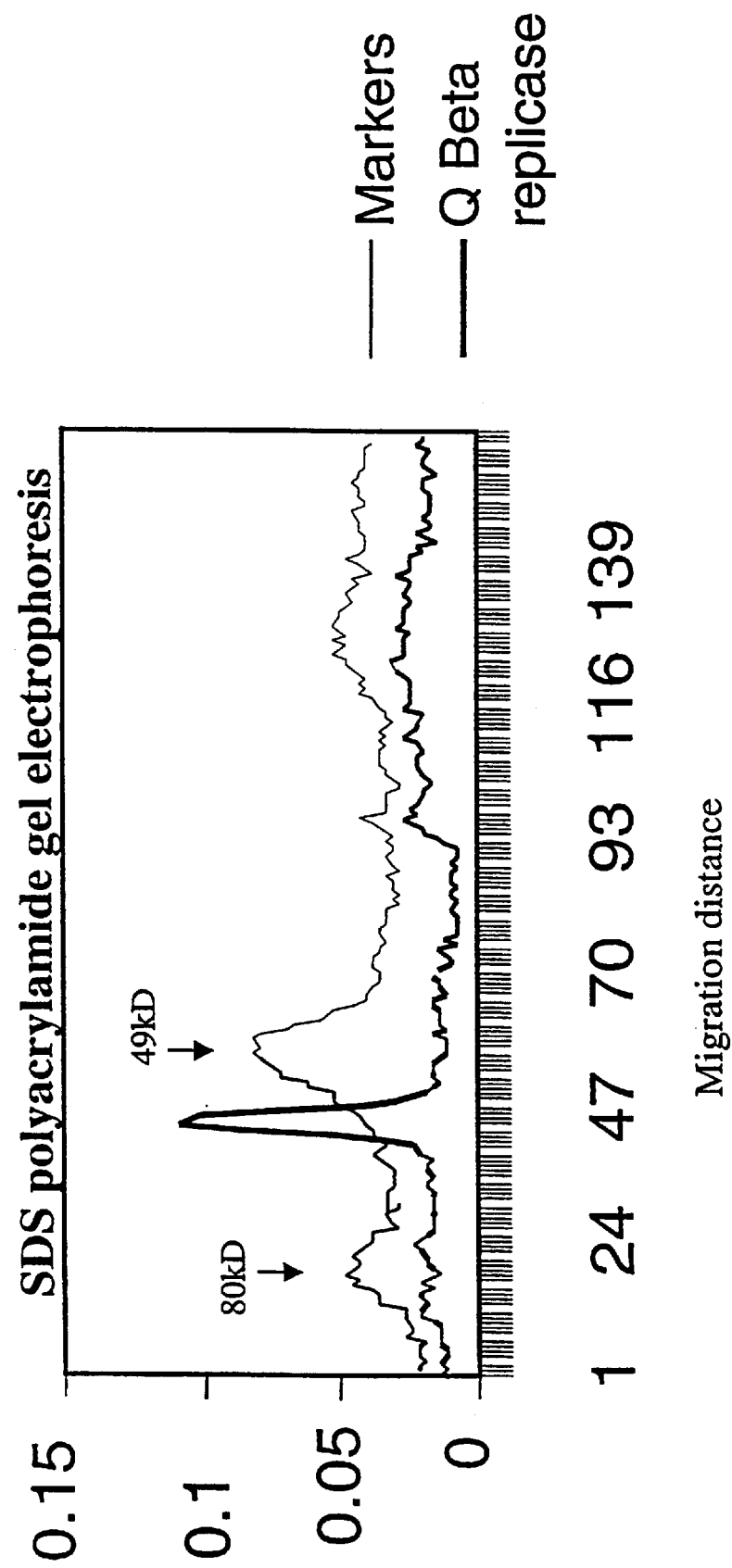
FIG. 12: Expression of the Qβ replicase in the rabbit reticulocyte coupled transcription/translation system

The reaction mix was incubated at 37° C. for 1 min. The reaction mixtures were dot blotted onto nylon membrane, e.g. hybond N, (only RNA or DNA bound to the enzyme Qb replicase will be retained on the membrane), washed with the 50 mM Tris HCl pH 7.4 containing 12 mM MgCl$_2$, UV cross linked onto the nylon membrane in the Stratalinker on the automatic setting. The BrightStar Biodetect kit was used for the detection of the biotinylated nucleic acid attached to the nylon membrane. FIG. 12 shows the assay of the eluted fractions from the DE52 column.

The active fractions were pooled, diluted with one volume buffer A and applied to a 35 ml column of DEAE-Sepharose FF, equilibrated to buffer A+0.1 M NaCl. The enzyme was eluted with a linear gradient of 0.1–0.4M NaCl in buffer A. The active fractions were pooled, the enzyme precipitated by addition of solid (NH$_4$)$_2$SO$_4$ (39 g/100 ml solution), collected by centrifugation and dissolved in 4 ml buffer B.

The enzyme was diluted until the conductivity was less than that of buffer B+0.2M NaCl and applied to a 100 ml column of Fractogel EMD SO3 equilibrated with buffer B, and eluted with a linear gradient (2 times 500 ml) of 0.2–0.8~M NaCl in buffer B. The active peaks, eluting at about 0.65M NaCl, were pooled, precipitated with solid (NH$_4$)$_2$SO$_4$ (39 g/100 ml solution), collected by centrifigation, and dissolved in 10 ml buffer A+50% glycerol. The solution was stored at –80° C.

The following steps were performed at small scale according to Sumper & Luce (1975). 4 mg Qβ replicase were applied to a 1.6×14.5 cm column of QAE-Sephadex~A-25 equilibrated with buffer A (diluted or dialysed to remove salt), and eluted with a 2×200 ml gradient of 0.05–0.25M NaCl in buffer A. The two clearly separated peaks of core and holoenzyme were pooled, diluted 1:1 with buffer A and applied to QAE-Sephadex columns, 2 ml for core, 6 ml for holo replicase, respectively, washed with buffer A+50% glycerol, and the replicase was eluted in concentrated form with buffer A+50% glycerol+0.2 M (NH$_4$)$_2$SO$_4$. The active fractions were stored at –80° C. Care was taken to avoid contamination of the equipment with RNA.

EXAMPLE 2

Cloning of Qβ Replicase Into the Eukaryotic Expression Vector pCDNA3.1

Figure 9:
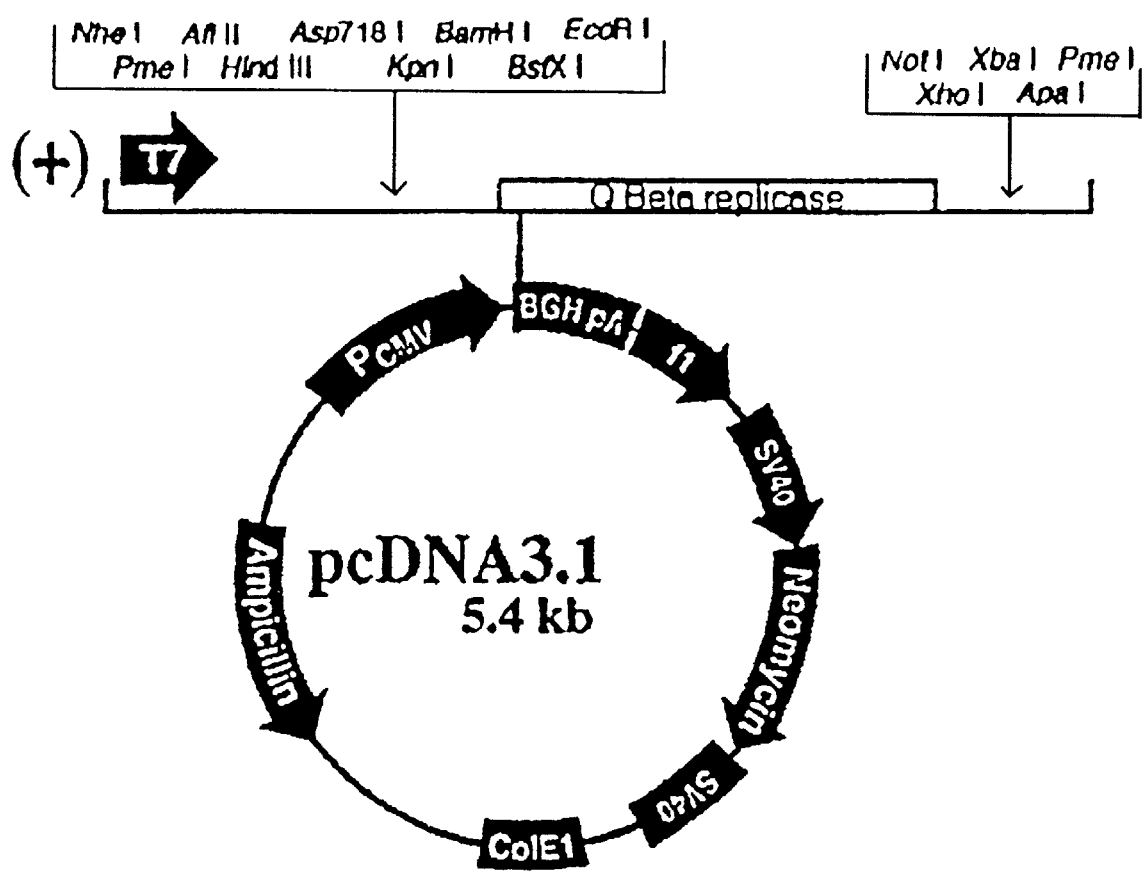
FIG. 9: Eukaryotic expression vector pcDNA3.1 for expression of Qβ replicase or Hepatitis C virus RNA dependent RNA polymerase in the rabbit reticulocyte coupled transcription/translation system.

Qβ replicase coding sequence was cloned into the eukaryotic expression vector pCDNA 3.1 (FIG. 9) to produce the vector named pCDNAQβ. This vector was used for the expression of Qβ replicase in situ in the coupled transcription/translation system and concomitant replication/mutation of target RNA. Sequence of oligonucleotides used as primers in PCR amplification of Qβ replicase for cloning into the EcoRI and NotI restriction sites in the eukaryotic expression vector pCDNA3.1 were:

5352 5'TCTGCAGAATTCGCCGCCACCAT-GTCTAAGACAGCATCTTCG (SEQ ID NO: 30);

5350 5'TTTATAARCTGCGGCCGCTTACGC-CTCGTGTAGAGACGC (SEQ ID NO: 31).

The coding sequence for the Qβ replicase b subunit was cloned into the pCDNA3.1 by standard molecular biology techniques (Sambrook et al., 1989). The cloned sequence was confirmed by DNA sequence analysis. Expression of the Qβ replicase in the rabbit reticulocyte coupled transcription/translation system was followed by the detection of biotinylated lysine (TRANSCEND, Promega) incorporated into the de novo synthesised Qβ replicase in the standard transcription/translation reaction as suggested by the commercial suppliers of the coupled transcription translation kits (Promega and Novagen) and the supplier of Transcend (Promega). At the completion of the incubation step of the coupled reaction, 20 µl of the reaction was heated to 90° C. with 2 ml of 10×SDS sample buffer and the samples subjected to SDS polyacrylamide gel electrophoresis (SDS-PAGE). This was followed by Western blotting and the de novo synthesised biotinylated Qβ replicase bands detected with TRANSCEND kit detection reagents. The results of this expression are shown in the gel scans of FIG. 12 where it can be seen that Qβ replicase has been synthesised shown by the biotinylated band at the correct size on the gel.

We then undertook coupled Transcription/translation reactions with the 1C3 template (example 3) but also expressing the Qβ replicase from pcDNA3.1 in the same reaction. The Qβ replicase synthesised in situ from the expression vector pCDNAQβ resulted in the increased synthesis of the 1C3 scFv in the coupled system in the presence of 0.5 mM manganese chloride; measured by incorporation of biotinylated lysine (FIG. 12b) as described above. The presence of the manganese chloride has previously been shown to relax the dependence of the Qβ replication activity on transcription/translation factors.

EXAMPLE 3

Construction by PCR of DNA Templates for Transcription

DNA sequences were amplified by standard and well-described techniques (Polymerase Chain Reaction [PCR] with specifically designed oligonucleotide primers, splice overlap extension, restriction enzyme digests etc) using either Taq, Tth, Tfl, Pwo or Pfu polymerase according to the supplier's instructions using either an FTS-1 thermal sequencer (Corbett Research), a PE2400 (PerkinElmer) or a Robocylcer gradient 96 (Stratagene). A list of oligonucleotide primers used is given in FIG. 11. Products were gel purified using BresaClean (Bresa) or used directly in coupled transcription and translation reactions.

Figure 7B:
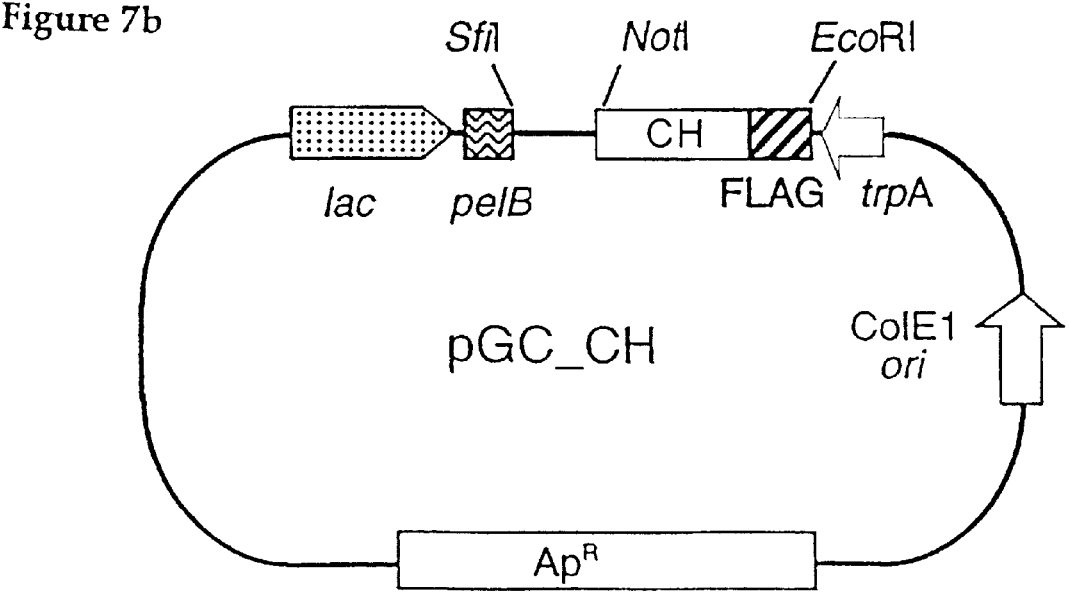

DNA sequences were amplified from starting templates which had been cloned into either vector pGC038CL (FIG. 7a) or pGC_CH (FIG. 7b) which provided an extension to the 3' terminus of the construct. This extension was either a constant region from a mouse monoclonal (1C3; Sequence FIG. 5a) or a constant region from a human IgM antibody (Sequence FIG. 5b). Forward (sense) primers (N5266 for the anti-GlyA scFv; N5517 or N5384, N5344 and N5343 for the anti-HepB scFv) used for amplification provided a transcriptional initiation site as well as a translational initiation site and ribosome binding site. Reverse (anitsense) primers (N5267 for the mouse constant region; N5385 for the human constant region) did not contain stop codons which allows the mRNA-ribosome-protein complex to remain associated. Both forward and reverse primers provided restriction enzyme sites (specifically SfiI and NotI, respectively) which enabled cloning of generated fragments.

Any of several promoter sequences for DNA dependent RNA polymerase can be used to direct transcription; however, the following sequences were the two preferred (these include translational initiation sequences; see below):

a) GCGCGAATACGACTCACTATAGAGGGA-CAAACCGCCATGGCC (SEQ ID NO: 32)
b) GCAGCTAATACGACTCACTATAGGAACA-GACCACCATGGCC (SEQ ID NO: 33)

These sequences have directed transcription of T7 DNA dependent RNA polymerase to produce RNA transcripts in two alternative formats of coupled transcription/translation systems.

Sequences encoding ribosome binding sites are known and have been included in the template upstream of the any one of the sequences of molecules of interest for ribosome display encoding either the scFv binding to glycophorin (1C3: FIG. 5c) or the scFv binding hepatitis B surface antigen (4C2; FIG. 5d). The same sequences have been included in the template upstream of any other sequences of interest for ribosome display (eg CTLA-4-based library sequences).

EXAMPLE 4
Coupled Transcription/translation and Ribosome Display in Rabbit Reticulocyte Lysate Cell Free System Transcription and translation was carried out in Siliconized Rnase-free 0.5 ml tubes (Ambion) using the TNT T7 coupled transcription/translation system (Promega) containing 0.5 mM magnesium acetate, 0.02 mM methionine and 3 mM oxidized glutathione (GSSG) (see Example 6, below) and the mixture was incubated at 60° C. for 90 min. In some reactions up to 10 mM reduced glutathione was also added. In reactions containing Qβ polymerase, the mixture also contained manganese chloride to a final concentration of 0.5 mM. After transcription and translation, the mixture was diluted with PBS and treated with DNaseI to remove any remaining starting DNA template. This was achieved by the addition of 40 mM Tris (pH 7.5), 6 mM $MgCl_2$ 10 mM NaCl and DNase I (Promega), followed by incubation at 30° C. for a further 20 min.

EXAMPLE 5
Selection of Ribosome Ternary Complex Displayed Proteins Against Antigens Using Dynabeads Tosylactivated Magnetic beads (Dynal) were coupled to GlycophorinA (GlyA; Sigma). HepatitisB Surface Antigen (HepB SA; BiosPacific, Emeryville, Calif. USA) or bovine serum albumin (BSA; Sigma) according to manufacturer's instructions. Where Streptavidin magnetic beads were used, these were coupled (according to manufacturer's instructions) to antigens (as shown above) which had been biotinylated using EZ-Link Sulfo-NHS-LC-Biotin (Pierce) according to manufacturer's instructions.

In order to select specifically binding mRNA-ribosome-protein complexes, 2–3 μl of antigen coupled (tosylactivated or streptavidin coated) magnetic beads were added to the final translation mixture and placed on a plate shaker (Raytek Instruments) at room temperature for 90 min with gentle shaking to prevent settling of the beads. The beads were recovered using a magnetic particle concentrator (Dynal) and these were washed three times with cold phosphate buffered saline (PBS) pH 7.4 containing 1% Tween and 5 mM magnesium acetate. The beads were then washed once with cold sterile water and finally resuspended in 10 μl of sterile water.

For the synthesis of cDNA from selected complexes, 2 μl of the final bead suspension was used in an RT-PCR reaction using either the Access RT-PCR system (Promega) or the Titan One-tube RT-PCR system (Boehringer Mannheim) according to manufacturer's instructions. The primers used for this reaction included the original forward (sense) primer (used to generate the starting template DNA primers; N5266 for the anti-GlyA scFv; N5517 or N5384, N5344 and N5343 for the anti-HepB scFv) and a negative (antisense) primer which was upstream of the original primer (N5268 and N5269 for mouse constant region constructs; N5386 and N5387 for human constant region constructs). In some cases, shorter primers (N5941 and N5942 for the anti-GlyA scFv-constant light region construct) were used to recover panned RNA templates.

For further cycles of selection, this DNA was gel purified (in some cases, simply diluted) and incorporated into in a further PCR using the forward and reverse primers which had been present in the original PCR to generate the starting DNA template. This new template could then be used in further selections as described above since it contained the appropriate initiation sites and is of the same length as the template in the first selection.

In order to show that the method described above can be used to select specific molecules, a single chain Fv (scFv) fused to a mouse constant light chain region which specifically binds to GlyA was amplified using primers which would allow the addition of a T7 transcriptional initiation site and a ribosome binding site. This template (T7-scFv) was used in a coupled transcription/translation reaction as described above and then split into three and mixed with either HepB SA, GlyA or BSA coupled magnetic beads. The beads were washed (as described above) and recovered mRNA-ribosome-protein complexes were used to synthesize cDNA. The results of this experiment showed the presence of a product of the correct size in each lane. The non-specific binding observed in the HepB SA and BSA lanes is probably due to aggregation of products synthesized during translation. It has been observed by others that only a proportion of products synthesized using the reticulocyte lysate are in a properly folded and active form. This problem was addressed in Example 6 below.

The GlyA specific product from this experiment was gel purified and re-amplified by PCR in order to synthesize more template for a further round of selection. A second round of panning showed predominantly a specific product in the sample probed with GlyA coupled magnetic beads. This showed that by the second round of selection, the products recovered were specific for GlyA.

EXAMPLE 6
Effect of Adding Oxidized and/or Reduced Glutathione

In a attempt to induce a higher proportion of correctly folded products during in vitro transcription and translation, various concentrations of either reduced or oxidized glutathione were added to the reaction mixture. The template used for these reactions was the anti-GlyA T7-scFv (as described above) and selections were performed using GlyA coupled magnetic beads. This experiment showed that the amount of recovered product increased with increasing concentrations of oxidized glutathione up to 5 mM. A further increase to 10 mM had a detrimental effect on the yield of recovered product. A concentration of around 2 mM oxidized glutathione was included in most transcriptions and translations.

Later results revealed that a further addition of 5 mM and 10 mM reduced glutathione to the reaction already containing 2 mM oxidized glutathione showed that the addition of 5 mM glutathione appeared to allow better folding of the displayed anti-GlyA scFv leading to an increased amount of recovered product from the GlyA panning over the control pannings. Further decreasing the concentration of reduced glutathione to to 0.5 mM showed similar effects.

EXAMPLE 7
Display of Mutation V-domain (CTLA-4) Library on Ribosomes

In order to show that ribosome display could be used to select binding elements from a polypeptide library, a library of CTLA4 mutants was ligated into plasmid pGC_CH (FIG. 7b) which allowed the addition of a constant heavy domain and this library was then amplified by PCR using primers N5659 and N5385 (FIG. 11). Primer N5659 was used to add the necessary upstream transcriptional and translational initiation sequences. This PCR DNA was then used as template for transcription and translation in a coupled cell free translation system using the methods described in Example 4. To demonstrate binding of mutant CTLA ribosome complexes, panning was performed using Hepatitis B surface antigen (HBSA), GlycophorinA (GlyA) and Bovine Serum Albumin (BSA) coated Dynabeads. RNA attached to bound complexes was then recovered by RT-PCR. The methods used for panning, selection and recovery was as described previously (Example 5).

Products corresponding approximately to the size of CTLA4 based mutants were recovered and showed that the CTLA4 library contained DNA encoding proteins which specifically bind HBSA, GlyA and BSA. These products were cloned into the vector pGC_CH (FIG. 7b) for DNA sequencing and expression of soluble products. Sequencing using standard methods (BigDye Terminator Cycle Sequencing; PE Applied Biosystems CA) showed that CTLA4-based specific inserts were present. Furthermore, expression analyses using ELISA showed that specifically reactive proteins were being expressed by the recombinant cultures. In these assays, recombinants which had been isolated by panning using GlyA-coated Dynabeads and screened by ELISA using GlyA-coated plates, gave stronger signals than similarly tested recombinants which had been isolated by panning using BSA-coated Dynabeads.

EXAMPLE 8
Effect of Including Qβ Replicase in Coupled Transcription and Translation In a attempt to both increase the yield of products, and increase the rate of mutagenesis in products during in vitro translation, Qβ replicase (in either of two forms) were added to the reaction mixture. The replicase was included as either a purified Qβ replicase protein or as a gene template under the control of a T7 transcriptional promoter (pCDNAQβ) which could be simultaneously synthesized during the coupled transcription/translation reaction. The template used for this reaction was again the anti-GlyA T7-scFv (as described above) and selections were performed using GlyA coupled magnetic beads These experiments showed that the amount of recovered GlyA reactive product increased (over the no Qβ replicase control) with the addition of purified Qβ replicase and, to a lesser extent, with the addition of Qβ replicase-encoding genomic template (pCDNAQβ).

In order to determine whether mutations had been inserted into the scFv sequence, the main product from each lane was gel isolated and purified. The DNA was digested with SfiI and NotI and ligated into similarly digested pGC vector and transformed into *E. coli* using standard protocols. DNA was isolated from recombinants from each series and six random clones from each series were subjected to DNA sequencing using standard methods (BigDye Terminator Cycle Sequencing; PE Applied Biosystems CA). Approximately 280 bases were sequenced from each clone and FIG. 14 shows the number and the position of mutations in these sequences. This experiment showed the introduction of an increased number of mutations after transcription and translation in the presence of Qβ replicase (in either of the forms used).

EXAMPLE 9
Addition of Artificial Qβ Sequences

In an attempt to increase the efficiency of Qβ replicase activity, specific Qβ binding sites were added to both the 5' and 3' ends of the anti-GlyA T7-scFv template by PCR. This new template (amplified with primers N5904 and N5910 [sense] and N5909 [anti-sense]; FIG. 11) was used in a coupled transcription/translation reaction which included Qβ replicase as either a purified Qβ replicase protein or as a gene template under the control of a T7 transcriptional promoter which could be simultaneously synthesized during the coupled transcription/translation reaction. Selections were performed using HepB, GlyA or BSA coupled magnetic beads and products recovered after RT-PCR. The presence of artificial Qβ stemloop sequences (i) did not have an adverse effect on coupled transcription, translation and selection and (ii) in most cases increased the amount of products recovered by RT-PCR after selection.

Figure 13:
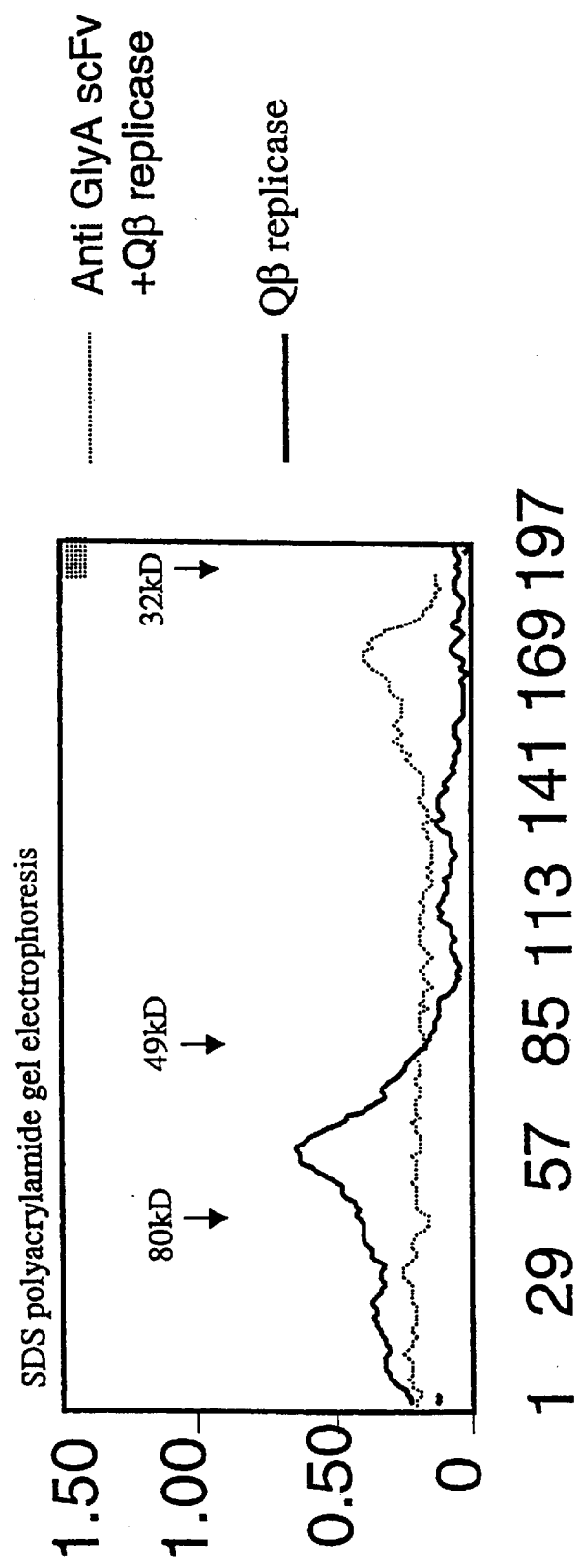
FIG. 13: Effect of Qβ replicase on coupled transcription/translation of anti GlyA 1C3 protein synthesis.
Figure 15:
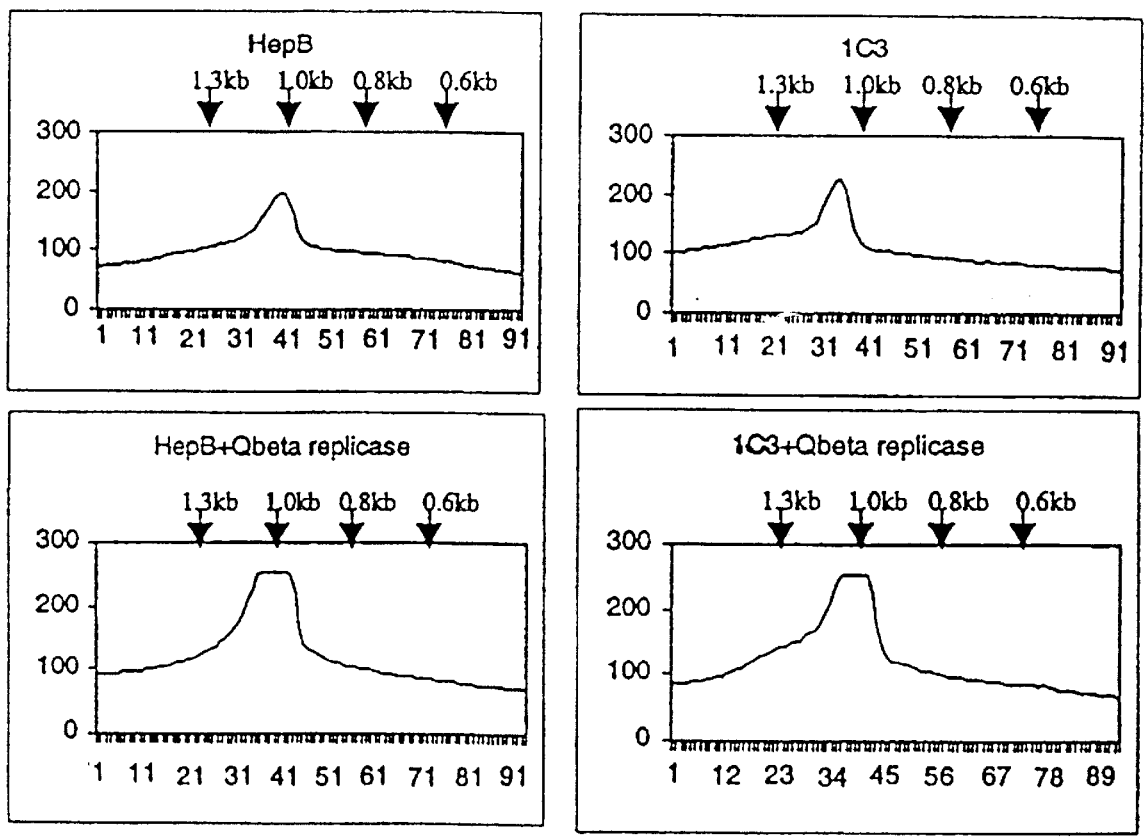
FIG. 15: Replication of anti glycophorin scFv transcripts by Qβ replicase in the coupled transcription/translation rabbit reticulocyte system: densitometer scanning.
Figure 17:
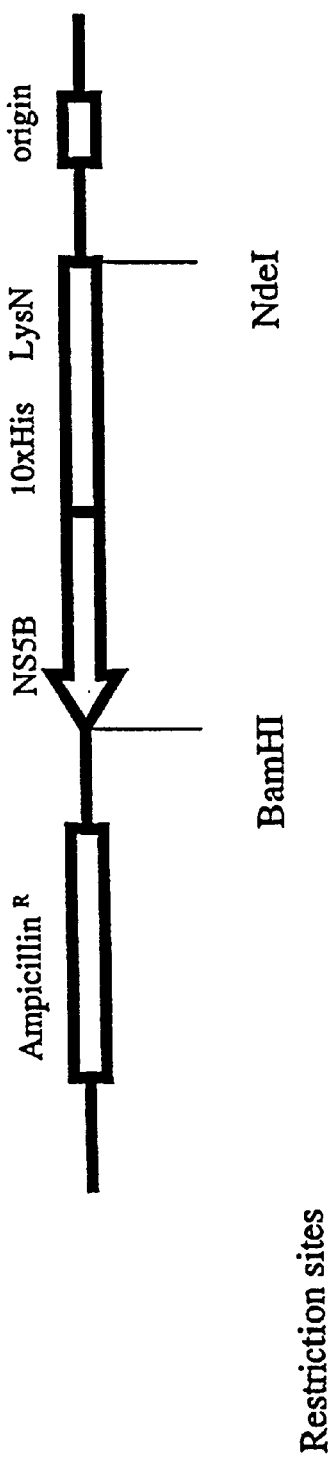
FIG. 17: Vector containing the Hepatitis C RNA dependent RNA polymerase.
Figure 18:
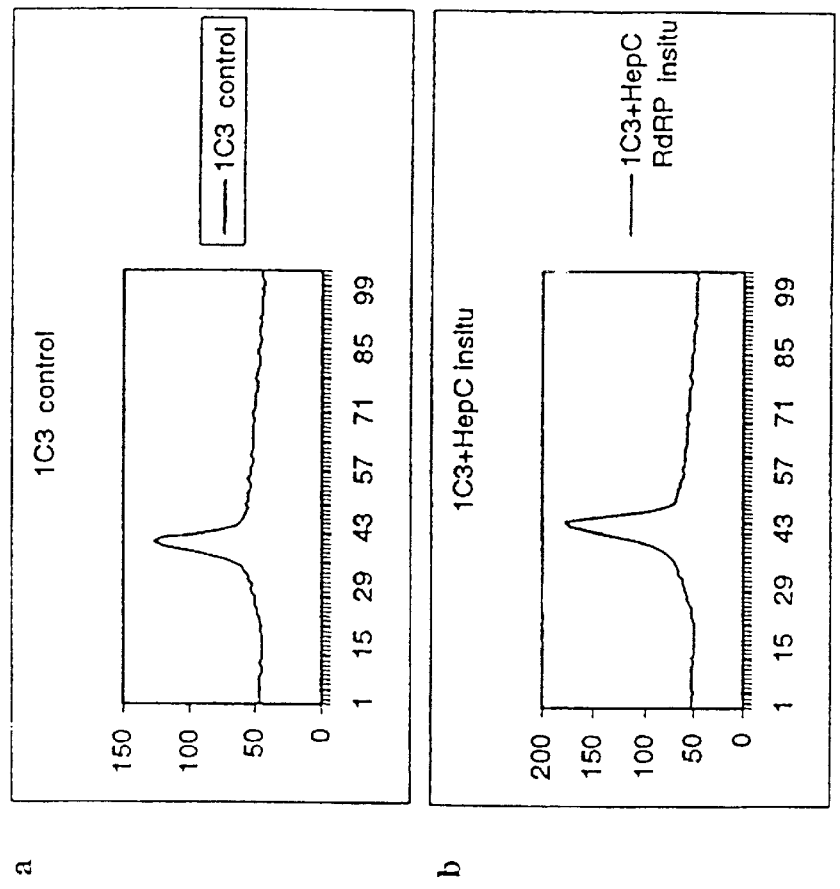
FIG. 18: Effect of Hepatitis C RNA dependent RNA polymerase expressed in the coupled transcription/translation system on replication of anti GlyA 1C3 scFv RNA. Agarose gel electrophoresis of the RT-PCR products stained with ethidium bromide and scanned.

EXAMPLE 10
Replication of Anti Glycophorin scFv Transcripts by Qb Replicase in the Coupled Transcription/translation Rabbit Reticulocyte System The T7-1C3 and T7-4C2 scFv templates for ribosome display were constructed as described in example 3 and subjected to coupled transcription/translation, under the following conditions. Standard coupled transcription/translation reactions were modified by the addition of Qβ replicase (purified as detailed in example 1). In a standard 20 μ reaction 1 ml of 20 μg/ml enzyme was added. Previously we have compared the effect of Qβ replicase concentration on replication of anti GlyA 1C3 scFv and anti Hepb 4C2 scFv in the coupled system and observed that 1 ml of this sample provided the optimum replication. Manganese chloride was added to a final concentration of 0.5 mM as this has been shown in published reports to decrease the requirement for transcription/translation factors. Reactions were allowed to continue for 2 hrs at 37° C. The replicated transcripts were analysed by RT-PCR after removing DNA template by DNAase I digestion in 40 mM Tris-HCl pH7.5, 6 mM MgCl$_2$, 10 mM NaCl at 30° C. for 20 mins. Standard phenol extraction was used to remove DNAaseI and other proteins. Samples were ethanol precipitated and the RNA precipitate dissolved in RNAase-free water. The RNA was assayed by RT-PCR using primers specific for each template, see example 3, and the PCR products (DNA) compared by agarose gel electrophoresis. The DNA bands were visualised by staining with ethidium bromide. The agarose gel was subjected to densitometry by scanning the digitised image with the gel-pro analyzer commercial software. FIG. 13 shows the densitometer traces of the agarose gel from which it can be seen that in the sample containing the purified Qβ replicase there is an increase in the amount of template produced.

EXAMPLE 11
Replication and Mutation of Anti Glycophorin scFv and Anti Hepatitis B scFv by Qβ Replicase from T7 Polymerase Transcripts; Qβ Replicase Mutates Transcripts During RNA Dependent RNA Replication Coupled transcription/translation reactions as detailed in previous examples were supplemented with Qβ replicase purified enzyme to replicate and mutate the T7 DNA dependent RNA polymerase transcribed anti GlyA 1C3 scFv RNA. Following the transcription/replication/mutation/translation incubation, the sample was treated wth DNAaseI and this enzyme removed as detailed in example 10. The purified RNA was then used as the template for RT-PCR reactions with anti GlyA 1C3 scFv-specific primers in the reaction as detailed in example 3. The thermostable polymerases used in these reactions were one of the high fidelity vent, pfu polymerase enzymes used in accordance with the manufacturers instructions. The PCR reaction products were purified with one of the commercially available kits as noted before and the purified DNA ligated into the commercially available plasmid pCRscript and transformed into competent E. coli XL1Blue cells using standard molecular biology techniques. The transformation reactions were plated onto YT-agar plates containing X-gal. After overnight incubation white colonies (E. coli with plasmids containing DNA inserts in the multi-cloning site) were picked and grown overnight at 37° C. in 5 ml of YT broth containing 100 $\mu$g/ml ampicillin. DNA was extracted from each of the cultures with the commercial kit (Quiagen) according to the manufacturer's instructions. The purified DNA was analysed by DNA sequencing; the sequencing results are displayed in FIG. 16. This table shows mutations in a random sample of sequences representing a minute sampling of mutations and sequence variation in the whole Q$\beta$ replicase replication/mutation reactions.

EXAMPLE 12

Predicted Secondary Structure of Template RNA

Figure 8:
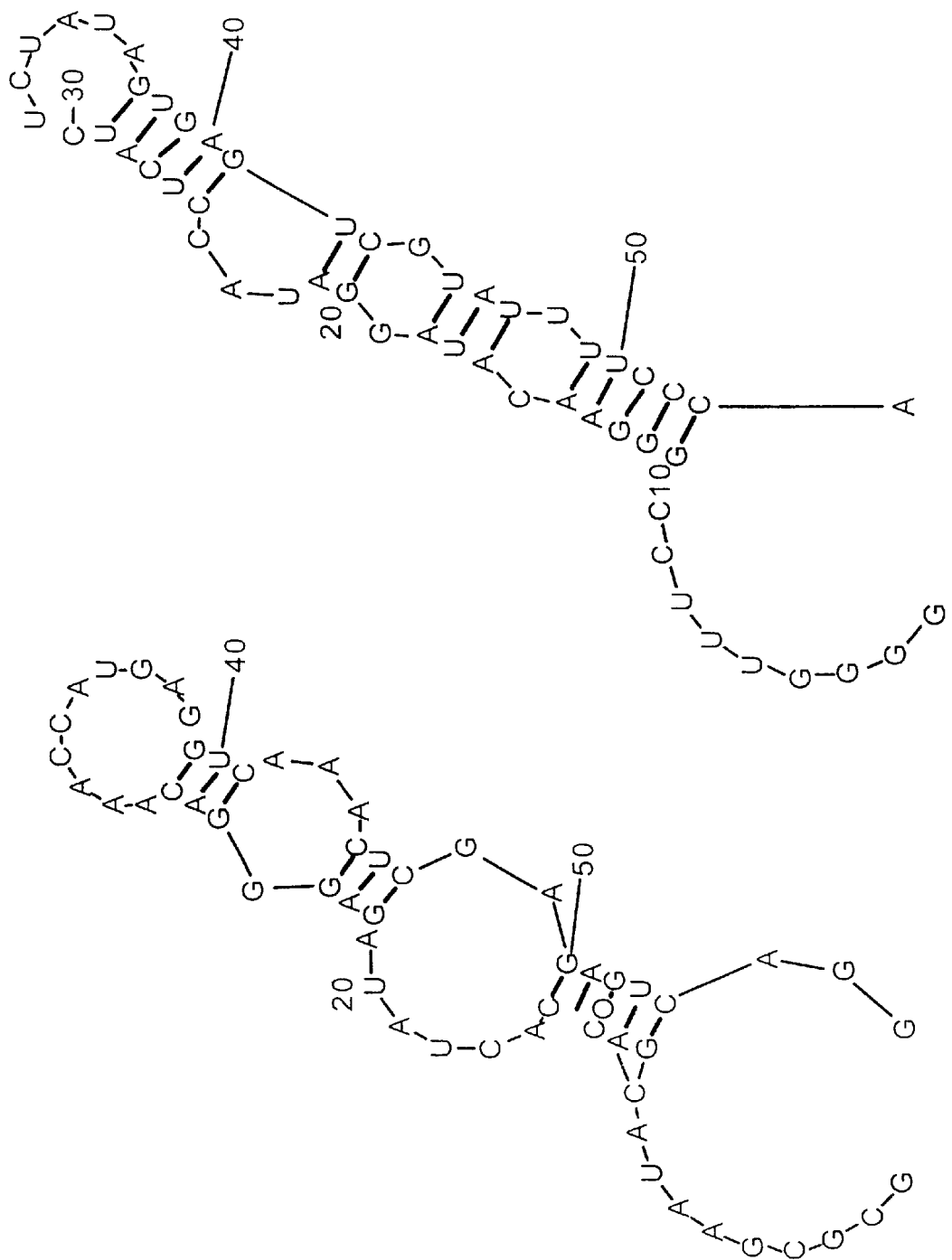
FIG. 8: Sequences of RNA fragments that form stem loop structures (SEQ ID NOS: 37 and 38).

The RNA sequences and putative secondary structures preferred by Q$\beta$ replicase for its RNA templates have been reported (Zamora et al., 1995). To determine whether these or related preferential structures exist in the templates for the continuous in vitro evolution the upstream untranslated sequences; T7 promoter sequences, the sequences encoding the 1C3 gene, the constant light anchor region gene, the anti hepb 4C2 scFv gene and the IgM human constant heavy anchor region gene were analysed with the Mfold program (Zucker et al 1991) and compared to the Q$\beta$ replicase preferred structures (as shown in FIG. 8). From this comparison it can be seen that the 1C3 scFv has been identified to have internal RNA secondary structure mimicing the M site structure of Q$\beta$ replicase, as does the CL anchor region and shows similarity to the preferred synthetic sequence reported by Zamora et al., 1995. This may explain the preferred replication of the anti GlyA 1C3 scFv CL template to that of the anti Hepb 4C2 scFVCH3 by Q$\beta$ replicase (see example 3). Therefore the CL region gene is proposed as an anchor region for displayed molecules for coupled transcription/translation display and any mutagenesis as the RNA encoding this region promotes and enhances Q$\beta$ replicase replication and associated mutation of this region and its genetic fusions.

EXAMPLE 13

Expression Protocol for pLysN-NS5B (83 kDa, pI~9.05)

pLysN-NS5B is a bacterial (cytoplasmic) expression vector with a T7 promotor. NS5B is the non-structural HepC RNA-dependent RNA-polymerase. NS5B is fused to a LysN moiety at its N terminus which are separated by a Gly-Ser-Gly-Ser-Gly linker. 10 His residues and followed by a Asp-Asp-Asp-Asp-Lys linker GSGSGHHHHHHHHHHD-DDDK (SEQ ID NO: 34)

This plasmid was transformed into E. coli strain HMS174 (DE3)pLysS and grown on 1YT/Amp$_{100\ \mu g/ml}$/Chloramphenicol$_{34\ \mu g/ml}$ agar plates at 37° C. A single colony was selected and cultured in an overnight broth 1YT/Amp$_{100\ \mu g/ml}$/Chloramphenicol$_{34\ \mu g/ml}$) at 37° C. For expression, the overnight starter culture was subcultured by dilution to an A600=0.1 in 1YT/Amp$_{100\ \mu g/ml}$/Chloramphenicol$_{34\ \mu g/ml}$) at 37° C. in 2 L shake flasks at 120 rpm. The culture was grown until the A600 reached 0.8–1.0 and then induced with 1 mM IPTG, supplemented with Amp100 $\mu$g/ml and expression allowed to proceed at 37° C. for 4–5 hours.

The culture was harvested and centrifuged 5000 g in a prechilled rotor at 4° C. The wet weight of the harvested culture was measured and the cell pellet frozen at –80° C. Approximately 3–4 grams was produced (wet weight) per liter of cell culture.

Lysis and Purification Protocol

Extraction of the HepC RdRp (NS5B) was achieved by lysing the cells followed by conventional protein chemistry techniques.

To the frozen cell pellet 5 ml of Buffer C (made fresh) at 4° C. was added per gram of cell pellet. The mixture was stirred at 4° C. using a magnetic bead until the culture was completely resuspended. The culture was then sonicated with 11 bursts each of 10 seconds with minute pause between each burst while continually stirring with a magnetic bead throughout the sonication process. The sonicated cells were centrifuged at 75000 g at 4° C. for 20 minutes and the supernatant (lysate) recovered.

A 30% saturation of AmSO$_4$ was added to the lysate and then centrifuged at 10000 g for 15 minutes. This acted to eliminate some bacterial proteins. The pellet was discarded and to the supernatant a 50% saturation of AmSO$_4$ was added and centrifuged and again at 10000 g for 15 minutes. This acted to precipitate the NS5B from a large proportion of E. coli proteins. The supernatant was discard and the pellet resuspended in half the original volume with Buffer C. This was dialysed in Buffer C at 4° C. overnight.

An aliquot from each step was analysed on SDS PAGE to confirm partial purification of ~90 kDa HepC RdRp band.

The dialysed extract was loaded onto a cation exchange column with Hyper D "S" resin pre-equilibrated with Buffer C. The column was then washed with Buffer C until a stable baseline was achieved. Elution was performed with a step gradient of Buffer C with 1M NaCl. It was found that NS5B eluted at a 50% NaCl ratio corresponding to a 600 mM NaCl concentration.

The eluted fractions were analysed on a 10% SDS PAGE to confirm purification. NS5B was purified by this process to over 90% homogeneity with minor smaller molecular weight contaminating proteins The purified NS5B was concentrated by 50% saturation with AmSO4 and resuspension in a volume of Buffer C (with Tris pH 7.4) sufficient to redissolve the pellet. This was then dialysed in the same buffer to eliminate the AmSO4.

This purity of the NS5B was such that further purification by size exlusion chromatography on a preparative Superose 12 column in Buffer C (Tris) was not necessitated, although optional.

| Buffers (Sonication Lysis, Elution, Dialysis) | Buffer C |
|---|---|
| 50 mM *** Na—PO4 pH6.8 Na2HPO4 | 2.32 ml |
| {or substitute for Tris pH 6.8 | |
| NaH2PO4 | 2.69 ml } |
| 100 mM NaCl | 0.5844 g |
| 10% Glycerol | 10 ml |
| 10 mM b-Mercaptoethanol | 70 $\mu$l |
| 0.02% NaN3 | 80 $\mu$l |
| 0.25M Sucrose | 8.56 g |
| 0.1% Detergent ($\beta$-Octyl Glucopyranoside) | 0.1 g |
| 1 mM Pefa-Eloc | 0.1 g |
| Complete ™ tablets(No EDTA) | 2 Tablets |
| H2O | to 100 ml |

SDS-Polyacrylamide gel electrophoresis (12.5% acrylamide) and coommassie blue staining of the proteins of the purified protein showed a single band at approximately 70 kD.

The HepC RdRp (NS5B) was assayed by numerous protocols. The simplest method relies on the Novagen Large Scale Transcription Kit (TB069). Modified forms of this protocol have been used successfully. This method is briefly described as follows.

A double stranded DNA template digested upstream of a T7/T3/SP6 promotor is used in the presence of a T7 DNA dependent RNA polymerase to make the RNA template. HepC RdRp (NS5B) in the same cocktail then amplifies the RNA produced by the T7 polymerase.

| | |
|---|---|
| DNA template (0.5 µg/ml) | 1 µl (0.5 ng) |
| ATP (20 mM) | 10 µl |
| CTP (20 mM) | 10 µl |
| GTP (20 mM) | 10 µl |
| UTP (20 mM) | 10 µl |
| 5X Transcription buffer | 20 µl |
| (400 mM HEPES pH7.5, 60 mM MgCl2, 50 mM NaCl) | |
| 1M DTT (1M) | 1 µl |
| T7 polymerase (100 U/ml) | 1 µl |
| HepC RdRp (NS5B) | x µl |
| Nuclease free water | y µl |

This method has utilised the control DNA template in the kit as well as plasmid DNA cut upstream of the T7 promotor successfully. The quantity of DNA used has been as low as 0.1 ng successfully. The quantity of T7 polymerase used has been as low as 0.1 µl.

Interestingly. the HepC RdRp (NS5B) in these experiments has been demonstrated to possess the capacity to prime off dsDNA in the absence of oligonucleotide primers and amplify RNA.

EXAMPLE 14

Cloning of Hepatitis C RNA Dependent RNA Polymerase Coding Sequence into the Eukaryotic Expression Vector pCDNA3.1

Hepatitis C RNA dependent RNA polymerase coding sequence FIG. 10 was cloned into the vector pCDNA3.1 (FIG. 9 ) for expression in situ in the coupled transcription/translation system and concomitant replication/mutation of target RNA. Sequence of oligonucleotides used as primers in PCR amplification of Hepatitis C RNA dependent RNA polymerase for cloning into the EcoRI and NotI restriction sites in the eukaryotic expression vector pCDNA3.1:

5' GTGGTGGAATTCGCCGCCACCTCTAT-GTCGTACTCTTGGACC (SEQ ID NO: 35)

5' GCACGGGCTTGGGCGATAATCCGCCGGC-GAGCTCAGATC (SEQ ID NO: 36)

Hepatitis C RNA dependent RNA polymerase was cloned into the pcDNA3.1 vector (named pCDNAHEPC) with a strategy similar to that described in example 2 but using the above oligonucleotides in the PCR amplification of the Hepatitis C RNA dependent RNA polymerase from the vector shown in FIG. 17. The methods used to demonstrate that the Hepatitis C RNA dependent RNA polymerase were being synthesised in situ were exactly as described in example 2. The results from the coupled reaction with the Hepatitis C RNA dependent RNA polymerase template in pCDNAHEPC are shown in FIG. 18. The results shown in this figure demonstrate that Hepatitis C RNA dependent RNA polymerase produces larger amounts of transcript (scan b) than T7 polymerase alone. Here the band has a greater intensity and is broader than the band without Hepatitis C RNA dependent RNA polymerase indicating the effect on the RNA.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

Baranov et al. (1989). Gene 84:463–466.

Baranov et al. (1993). Methods in Enzymology 217:123–142.

Barbas et al. (1994). Ann Rev Imm 57, 191

Barrera et al. (1993). J. Mol. Biol. 232, 512–521.

Brown and Gold (1995a). Biochemistry 34, 14775–14782.

Brown and Gold (1995b). Biochemistry 34, 14765–14774.

Brown and Gold (1996). Proc. Natl. Acad. Sci. (USA) 93, 11558–11562.

Coia et al. (1996). J. Immunol. Meth. 192, 13–23.

Deiman et al (1997). J. Virol. 71, 5990.

Duenas and Borrebaeck (1994). Bio/Technology 12, 999–1002.

Ghee et al. (1996). J. Mol. Biol. 261, 222–230.

Gram et al. (1992). PNAS 89, 3586.

Hanes and Pluckthun (1997). Proc. Natl. Acad. Sci. (USA) 94, 4937–4942.

He and Taussig (1997). Nucleic Acids Research 25, 5132–5134.

Irving et al (1996). Immunotechnology 2, 127–143.

Keiler et al. (1996). Science 271, 990–993.

Kigawa et al. (1991). J. Biochem. 110, 166–168.

Kolosov et al. (1992). Biotechnology and Applied Biochemistry 16, 125–133.

Kramer et al. (1978). Proc. Natl. Acad. Sci. (USA) 75, 5334–5338.

Krebber et al. (1995). FEBS Lett. 377, 227–331.

Kudlicki et al. (1992). Analytical Biochemistry 206, 389–393.

Lizardi et al. (1988). Bio/Technology 6, 1197–1202.

Mattheakis et al. (1994). Proc. Natl. Acad. Sci. (USA) 91, 9022–9026.

Melton et al. (1984a). Nucleic Acid Res. 12: 7035–56.

Melton et al. (1984b). Nucleic Acid Res. 12: 7057–7070.

Morozov et al. (1993). PNAS 90, 9325–9329.

Munishkin et al. (1991). J. Mol. Biol. 221, 463–472.

Nishihara et al. (1983). J.Biochem. (Tokyo) 93, 669–674.

Ojala P M and Bamford D H (1995) Virology, 207, 400.

Rattat et al. (1990). Tibtech 8, 275–276.

Rohde et al. (1995). J Mol Biol 249, 754–762.

Ryabova et al. (1989). Nucleic Acids Research 17, 4412.

Ryabova et al. (1989). Nucleic Acids Research 17, 4412.

Rvabova et al. (1994). Journal of Biological Chemistry 269, 1501–1506.

Ryabova et al. (1997). Nature Biotechnology, 15, 79–84.

Sambrook et al. (1989). In: Nolan, C. (Ed.), Molecular Cloning: A Laboratory Manual, 2nd edn. Cold Spring Harbor Laboratory Press, Cold Spring Harbor, N.Y.

Spirin (1990a) U.S. Pat. Nos. 5,556,769; 5,643,768;

Spirin (1990b). pp. 56–70 in THE RIBOSOME: STRUCTURE, FUNCTION and EVOLUTION (eds. Hill, W. E., et al.), Amer. Soc. Microbiol., Washington, D.C.

Spirin et al. (1988). Science 242, 1162–1164.

Spirin, A. S. (1991). pp 31–43 in FRONTIERS IN BIOPROCESSING II (eds. Todd, P. et al.), Amer. Chem. Soc., Washington, D.C.

Stemmer (1994). Nature 370, 389–391.

Stemmer et al. (1995). Science 270, 1510,

Sumper and Luce (1975). Proc. Natl. Acad. Sci. (USA) 72, 162–166.

Winter et al. (1994). Ann Rev Biochem 12, 433,
Winter et al. (1994). Ann. Rev. Biochem. 12, 433.
Yang et al (1995). J Mol Biol 254, 392

Zamora et al. (1995). Biochemistry, 34, 1261–1266.
Zubay (1973). Ann. Rev. Genetics 7, 267–287
Zucker (1991) Nucleic Acids Res 25; 2707–14

What is claimed is:

1. A method for the mutation, synthesis and selection of a protein which binds to a target molecule, the method comprising:
    (a) incubating a replicable mRNA molecule encoding the protein with ribonucleoside triphosphate precursors of RNA and an RNA-directed RNA polymerase, wherein the RNA-directed RNA polymerase replicates the mRNA molecule but introduces mutations thereby generating a population of mutant mRNA molecules;
    (b) incubating the mutant mRNA molecules from step (a) with a translation system under conditions which result in the synthesis of a population of mutant proteins such that after translation, mutant proteins are linked to their encoding mRNA molecules thereby forming a population of mutant protein/mRNA complexes;
    (c) selecting one or more mutant protein/mRNA complex (es) by exposing the population of mutant protein/mRNA complexes from step (b) to a target molecule and recovering the mutant protein/mRNA complex(es) bound thereto; and
    (d) optionally releasing the mRNA molecules from the complex(es),
wherein step (b) follows step (a), and wherein step (c) follows step (b).

2. A method for the mutation, synthesis and selection of a protein which binds to a target molecule, the method comprising:
    (a) incubating a replicable mRNA molecule encoding the protein with ribonucleoside triphosphate precursors of RNA and an RNA-directed RNA polymerase, wherein the RNA-directed RNA polymerase replicates the mRNA molecule but introduces mutations thereby generating a population of mutant mRNA molecules;
    (b) incubating the mutant mRNA molecules from step (a) with a translation system under conditions which result in the synthesis of a population of mutant proteins such that after translation, mutant proteins are linked to their encoding mRNA molecules thereby forming a population of mutant protein/mRNA complexes;
    (c) selecting one or more mutant protein/mRNA complex (es) by exposing the population of mutant protein/mRNA complexes from step (b) to a target molecule;
    (d) repeating steps (a) to (c) one or more times, wherein the replicable mRNA molecule used in step (a) is the mRNA obtained from complex(es) selected in step (c);
    (e) recovering mutant protein complexes bound to the target molecule(s);and
    (f) optionally releasing or recovering the mRNA molecules from the complex(es),
wherein step (b) follows step (a), wherein step (c) follows step (b), wherein step (d) follows step (c), and wherein step (e) follows step (d).

3. A method as claimed in claim 2 in which step (d) is repeated more than once.

4. A method as claimed in claim 1 in which the mutant proteins are linked to their encoding mRNA molecules via ribosome complexes.

5. A method as claimed in claim 1 in which steps (a) to (d) are carried out simultaneously in either a single or multiple chambered vessel, wherein the multiple chambered vessel allows the transfer of fluids between chambers.

6. A method as claimed in claim 1 in which the RNA-directed RNA polymerase
    (i) introduces mutations into the replicated RNA molecule at a frequency of at least one point mutation in $10^4$ bases; or
    (ii) introduces at least one insertion or deletion at a frequency of $10^{-4}$.

7. A method as claimed in claim 1 in which the RNA-directed RNA polymerase
    (i) introduces mutations into the replicated RNA molecule at a frequency of at least one point mutation in $10^3$ bases; or
    (ii) introduces at least one insertion or deletion at a frequency of $10^{-3}$.

8. A method as claimed in claim 1 in which the RNA-directed RNA polymerase is selected from the group consisting of Qβ replicase, Hepatitis C RNA-directed RNA polymerase, Vesicular Stomatitis Virus RNA-directed RNA polymerase, Turnip yellow mosaic virus replicase and RNA bacteriophage phi 6 RNA-dependent RNA.

9. A method as claimed in claim 1 in which the RNA-directed RNA polymerase is Qβ replicase.

10. A method as claimed in claim 1 in which the translation system is a cell-free translation system.

11. A method as claimed in claim 10 in which the cell-free translation system comprises an S-30 extract from *Escherichia coli*.

12. A method as claimed in claim 10 in which the cell-free translation system comprises a reticulocyte lysate.

13. A method as claimed in claim 1 in which the translation system comprises oxidised and/or reduced glutathione at a total concentration of between 0.1 mM and 10 mM.

14. A method as claimed in claim 13 in which the glutathione concentration is between 2 mM and 7 mM.

15. A method as claimed in claim 13, in which the translation system comprises oxidized glutathione at a concentration of about 2 mM and reduced glutathione at a concentration of between 0.5 mM and 5 mM.

16. A method as claimed in claim 1, in which the replicable mRNA molecule is derived from a template selected from the group consisting of RQ135 RNA, MDV-1 RNA, microvariant RNA, nanovariant RNAs, CT-RNA and RQ120 RNA.

17. A method as claimed in claim 1, in which the replicable mRNA molecule is derived from a vector which comprises a template selected from MDV-1 RNA and RQ135 RNA.

18. A method as claimed in claim 1, which further comprises the step of transcribing a DNA template to produce the replicable mRNA.

19. A method as claimed in claim 18 in which the DNA template is a linear DNA molecule.

20. A method as claimed in claim 18 in which the DNA template comprises:
    (i) an untranslated region including a control element which promotes transcription of the DNA into mRNA and a ribosome binding site;
    (ii) an open reading frame encoding the protein which binds to the target molecule; and
    (iii) a stemloop structure situated upstream of the open reading frame.

21. A method as claimed in claim 20 in which the stemloop structure is a replicase binding sequence.

22. A method as claimed in claim 21 in which the replicase binding sequence is between 15 to 50 nucleotides in length.

23. A method as claimed in claim 21 in which the replicase binding sequence is between 20 and 40 nucleotides in length.

24. A method as claimed in claim 21 in which the replicase binding sequence is recognised by Qβ replicase.

25. A method for the mutation, synthesis and selection of a protein which binds to a target molecule, the method comprising:
  (a) transcribing a DNA template to produce a replicable mRNA, in which the DNA template comprises:
    (i) an untranslated region including a control element which promotes transcription of the DNA into mRNA and a ribosome binding site;
    (ii) an open reading frame encoding the protein which binds to the target molecule; and
    (iii) a stemloop structure, which is a replicase binding sequence comprising the sequence: GGGACACGAAAGCCCCAGGAACCUUUCG (SEQ ID NO: 27), situated upstream of the open reading frame;
  (b) incubating the replicable mRNA molecule encoding the protein with ribonucleoside triphosphate precursors of RNA and an RNA-directed RNA polymerase, wherein the RNA-directed RNA polymerase replicates the mRNA molecule but introduces mutations thereby generating a population of mutant mRNA molecules;
  (c) incubating the mutant mRNA molecules from step (a) with a translation system under conditions which result in the synthesis of a population of mutant proteins such that after translation, mutant proteins are linked to their encoding mRNA molecules thereby forming a population of mutant protein/mRNA complexes;
  (d) selecting one or more mutant protein/mRNA complex(es) by exposing the population of mutant protein/mRNA complexes from step (b) to a target molecule and recovering the mutant protein/mRNA complex(es) bound thereto; and
  (e) optionally releasing the mRNA molecules from the complex(es),
wherein step (b) follows step (a), wherein step (c) follows step (b), and wherein step (d) follows step (c).

26. A method as claimed in any one of claims 20 to 24 in which a second stemloop structure is included downstream of the open reading frame.

27. A method as claimed in claim 20 in which the ribosome binding site is derived from the MS2 virus.

28. A method as claimed in claim 20, in which the DNA template further comprises a sequence encoding a polypeptide, fused 3' and in frame with the open reading frame.

29. A method for the mutation, synthesis and selection of a protein which binds to a target molecule, the method comprising:
  (a) transcribing a DNA template to produce a replicable mRNA, in which the DNA template comprises:
    (i) an untranslated region including a control element which promotes transcription of the DNA into mRNA and a ribosome binding site;
    (ii) an open reading frame encoding the protein which binds to the target molecule;
    (iii) a sequence encoding an immunoglobulin constant region, fused 3' and in frame with the open reading frame; and
    (iv) a stemloop structure situated upstream of the open reading frame;
  (b) incubating the replicable mRNA molecule encoding the protein with ribonucleoside triphosphate precursors of RNA and an RNA-directed RNA polymerase, wherein the RNA-directed RNA polymerase replicates the mRNA molecule but introduces mutations thereby generating a population of mutant mRNA molecules;
  (c) incubating the mutant mRNA molecules from step (a) with a translation system under conditions which result in the synthesis of a population of mutant proteins such that after translation, mutant proteins are linked to their encoding mRNA molecules thereby forming a population of mutant protein/mRNA complexes;
  (d) selecting one or more mutant protein/mRNA complex(es) by exposing the population of mutant protein/mRNA complexes from step (b) to a target molecule and recovering the mutant protein/mRNA complex(es) bound thereto; and
  (e) optionally releasing the mRNA molecules from the complex(es),
wherein step (b) follows step (a), wherein step (c) follows step (b), and wherein step (d) follows step (c).

30. A method as claimed in claim 29 in which the immunoglobulin constant domain is a constant light domain of the mouse antibody 1C3.

31. A method as claimed in claim 1, in which the target molecule is selected from a DNA molecule, a protein, a receptor, a cell surface molecule, a metabolite, an antibody, a hormone, a bacterium or a virus.

32. A method as claimed in claim 1, in which the target molecule is bound to a matrix.

33. A method as claimed in claim 32, in which the matrix comprises magnetic beads.

34. A method for the mutation, synthesis and selection of a protein which binds to a target molecule, the method consisting essentially of:
  (a) incubating a replicable mRNA molecule encoding the protein with ribonucleoside triphosphate precursors of RNA and an RNA-directed RNA polymerase, wherein the RNA-directed RNA polymerase replicates the mRNA molecule but introduces mutations thereby generating a population of mutant mRNA molecules;
  (b) incubating the mutant mRNA molecules from step (a) with a translation system under conditions which result in the synthesis of a population of mutant proteins such that after translation, mutant proteins are linked to their encoding mRNA molecules thereby forming a population of mutant protein/mRNA complexes;
  (c) selecting one or more mutant protein/mRNA complex(es) by exposing the population of mutant protein/mRNA complexes from step (b) to a target molecule and recovering the mutant protein/mRNA complex(es) bound thereto; and
  (d) optionally releasing the mRNA molecules from the complex(es),
wherein step (b) follows step (a), and wherein step (c) follows step (b).

35. A method for the mutation, synthesis and selection of a protein which binds to a target molecule, the method consisting essentially of:
  (a) incubating a replicable mRNA molecule encoding the protein with ribonucleoside triphosphate precursors of RNA and an RNA-directed RNA polymerase, wherein the RNA-directed RNA polymerase replicates the mRNA molecule but introduces mutations thereby generating a population of mutant mRNA molecules;
  (b) incubating the mutant mRNA molecules from step (a) with a translation system under conditions which result in the synthesis of a population of mutant proteins such that after translation, mutant proteins are linked to their encoding mRNA molecules thereby forming a population of mutant protein/mRNA complexes;
  (c) selecting one or more mutant protein/mRNA complex(es) by exposing the population of mutant protein/mRNA complexes from step (b) to a target molecule;

(d) repeating steps (a) to (c) one or more times, wherein the replicable mRNA molecule used in step (a) is the mRNA obtained from complex(es) selected in step (c);

(e) recovering mutant protein complexes bound to the target molecule(s); and (f) optionally releasing or recovering the mRNA molecules from the complex(es), wherein step (b) follows step (a), wherein step (c) follows step (b), wherein step (d) follows step (c), and wherein step (e) follows step (d).

36. A method for the mutation, synthesis and selection of a protein which binds to a target molecule, the method comprising:

(a) incubating a replicable mRNA molecule encoding a known protein with ribonucleoside triphosphate precursors of RNA and an RNA-directed RNA polymerase, wherein the RNA-directed RNA polymerase replicates the mRNA molecule but introduces mutations thereby generating a population of mutant mRNA molecules;

(b) incubating the mutant mRNA molecules from step (a) with a translation system under conditions which result in the synthesis of a population of mutant proteins such that after translation, mutant proteins are linked to their encoding mRNA molecules thereby forming a population of mutant protein/mRNA complexes;

(c) selecting one or more mutant protein/mRNA complex(es) by exposing the population of mutant protein/mRNA complexes from step (b) to a target molecule and recovering the mutant protein/mRNA complex(es) bound thereto; and (d) optionally releasing the mRNA molecules from the complex(es), wherein step (b) follows step (a), and wherein step (c) follows step (b).

37. A method for the mutation, synthesis and selection of a protein which binds to a target molecule, the method comprising:

(a) providing a DNA template comprising a sequence encoding a protein;

(b) transcribing the DNA template to produce replicable mRNA molecules encoding the protein;

(c) incubating the replicable mRNA molecules encoding the protein with ribonucleoside triphosphate precursors of RNA and an RNA-directed RNA polymerase, wherein the RNA-directed RNA polymerase replicates the mRNA molecule and introduces mutations therein, thereby generating a population of mutant mRNA molecules;

(d) incubating the mutant mRNA molecules from step (c) with a translation system under conditions which result in the synthesis of a population of mutant proteins such that after translation, mutant proteins are linked to their encoding mRNA molecules thereby forming a population of mutant protein/mRNA complexes;

(e) selecting one or more mutant protein/mRNA complex(es) by exposing the population of mutant protein/mRNA complexes from step (b) to a target molecule and recovering the mutant protein/mRNA complex(es) bound thereto; and (f) optionally releasing the mRNA molecules from the complex(es), wherein step (b) follows step (a), wherein step (c) follows step (b), wherein step (d) follows step (c) and wherein step (e) follows step (d).

38. The method of claim 37 including step (f) and further comprising recycling released mRNA molecules to step (c).

* * * * *

UNITED STATES PATENT AND TRADEMARK OFFICE
CERTIFICATE OF CORRECTION

PATENT NO. : 6,562,622 B1 Page 1 of 1
DATED : May 13, 2003
INVENTOR(S) : Coia et al.

It is certified that error appears in the above-identified patent and that said Letters Patent is hereby corrected as shown below:

<u>Title page,</u>
Item [22] PCT Filed, change "1997" to -- 1999 --.

Signed and Sealed this

Fifteenth Day of February, 2005

JON W. DUDAS
*Director of the United States Patent and Trademark Office*

SEQUENCE LISTING

<160> NUMBER OF SEQ ID NOS: 38

<210> SEQ ID NO 1
<211> LENGTH: 318
<212> TYPE: DNA
<213> ORGANISM: Murine sp.
<220> FEATURE:
<221> NAME/KEY: misc_feature
<222> LOCATION: (1)..(318)
<223> OTHER INFORMATION: Sequence of the constant light region of mouse
      monoclonal antibody 1C

<400> SEQUENCE: 1

```
gctgatgctg caccaactgt atccatcttc ccaccatcca gtgagcagtt aacatctgga      60
ggtgcctcag tcgtgtgctt cttgaacaac ttctacccca aagacatcaa tgtcaagtgg     120
aagattgatg gcagtgaacg acaaaatggc gtcctgaaca gttggactga tcaggacagc     180
aaagacagca cctacagcat gagcagcacc ctcacgttga ccaaggacga gtatgaacga     240
cataacagct atacctgtga ggccactcac aagacatcaa cttcacccat tgtcaagagc     300
ttcaacaggg gagagtgt                                                   318
```

<210> SEQ ID NO 2
<211> LENGTH: 324
<212> TYPE: DNA
<213> ORGANISM: Homo sapiens
<220> FEATURE:
<221> NAME/KEY: misc_feature
<222> LOCATION: (1)..(324)
<223> OTHER INFORMATION: Sequence of the human constant heavy chain

<400> SEQUENCE: 2

```
gcagatcaag acacagccat ccgggtcttc gccatccccc catcctttgc cagcatcttc      60
ctcaccaagt ccaccaagtt gacctgcctg gtcacagacc tgaccaccta tgacagcgtg     120
accatctcct ggacccgcca gaatggcgaa gctgtgaaaa cccacaccaa catctccgag     180
agccacccca tgccactttt cagcgccgtg ggtgaggcca gcatctgcga ggatgactgg     240
aattccgggg agaggttcac gtgcaccgtg acccacacag acctgccctc gccactgaag     300
cagaccatct cccggcccaa gggc                                            324
```

<210> SEQ ID NO 3
<211> LENGTH: 748
<212> TYPE: DNA
<213> ORGANISM: Homo Sapeins
<220> FEATURE:
<221> NAME/KEY: misc_feature
<222> LOCATION: (1)..(748)
<223> OTHER INFORMATION: Sequence of the anti-glycophorin (1C3) scFv

<400> SEQUENCE: 3

```
atggccgagg tgaggcttct tgagtctgga ggtggcccgg tacaacctgg aggatccctg      60
aaactctcct gtgcagcctc aggattcgat tttagtagat actggatgaa ttgggtccgg     120
cgggctccag ggaagggct agagtggatt ggagaaatta tcaacaaag cagtacgata      180 aactattcgc cacctctgaa ggataaattc atcatctcca gagacaacgc caaaagtacg     240
ctgtacctgc aaatgaacaa agtgagatct gaggacacag cccctttatta ttgtgcaaga   300
```

```
ctttctctta ctgcggcagg gtttgcttac tggggccaag ggactctggt caccgtcgcc      360
tccggtggtg gtggttcagg aggaggaggt tcggtggtg gtggttcgga catcgtcatg       420
tcacagtctc catcctccct ggctgtgtca gtaggagaga aggtcactat gagctgcaga      480
tccagtcaga gtctgttcaa cagtagaacc cgaaagaact acttgacttg gtaccagcag     540
aaaccagggc agtctcctaa accgctgatc tactgggcat ccactaggga atctggggtc     600
cctgatcgct tcacaggcag tggatctggg acagatttca ctctcaccat cagcagtgtg     660
caggctgaag acctggcaga ttattactgc aagcaatctt ataatcttcg gacgttcggt     720
ggaggcacca agctggaaat caaacggg                                         748

<210> SEQ ID NO 4
<211> LENGTH: 807
<212> TYPE: DNA
<213> ORGANISM: Homo Sapeins
<220> FEATURE:
<221> NAME/KEY: misc_feature
<222> LOCATION: (1)..(807)
<223> OTHER INFORMATION: Sequence of the anti-hepatitis surface antigen
      (4C2) scFv

<400> SEQUENCE: 4
ccatggccga tgtgaagctt caggagtcag gcctgagct ggtgaggccc ggggtctcag        60
tgaagattac ctgcaaggt tccggctaca cattcactga ttatgctatg cattgggtga      120
agcagagtca tgccaagagt ctagagtgga ttggacttat tagtaattcc tttggtaata     180
caaactacaa ccagaagttt gaggccaagg ccacaatgac tgtagacaaa tcctccaaca     240
caggctattt ggaacttggc agattgacat ctgaggattc tgccatctat tactgtgcaa     300
gagtgatcga ctggtccttc gatgtctggg gccaagggac cacggtcacc gtctcctcag     360
gtggaggcgg ttcaggcgga ggtggctctg gcggtggcgg atcggacatt gtgctgaccc     420
aatctccagc aatcatgttc gcatctccag gggagaaggt caccatgacc tgcagtgcca     480
actcacgtgt caggtacgtg cactggtacc aacagaagtc aggcacctcc cccaaaagat     540
ggatttatga cacatccaaa ctggcttctg gagtccctgc tcgcttcagt ggcagtgggt     600
ctgggacctc tcactctctc acaatcagca gcttggaggc tgaagatgct gccacttatt     660
actgccagca ctggagtagt aaccctccca cgttcggtgc tgggaccaag ctggaaataa     720
aacgggcggc cgcagattat aaagatgatg atgataaagc cgcggcccat caccaccatc     780
accattaaga attcagcccg cctaatg                                          807

<210> SEQ ID NO 5
<211> LENGTH: 7489
<212> TYPE: DNA
<213> ORGANISM: Artificial
<220> FEATURE:
<223> OTHER INFORMATION: plasmid pBRT7Q beta

<400> SEQUENCE: 5
ggggaccccc tttaggggt cacctcacac agcagtactt cactgagtat aagaggacat        60
atgcctaaat taccgcgtgg tctgcgtttc ggagccgata tgaaaattct taatgatttt     120
caggagctct ggttccaga cctctttatc gaatcttccg acacgcatcc gtggtacaca      180
ctgaagggtc gtgtgttgaa cgcccacctt gatgatcgtc tacctaatgt aggcggtcgc     240
caggtaaggc gcactccaca tcgcgtcacc gttccgattc ctcttcagg ccttcgtccg      300 gtaacaaccg ttcagtatga tcccgcagca ctatcgttct tattgaacgc tcgtgttgac     360
```

```
tgggatttcg gtaatggcga tagtgcgaac cttgtcatta atgactttct gtttcgcacc      420
tttgcaccta aggagtttga tttttcgaac tccttagttc ctcgttatac tcaggccttc      480
tccgcgttta atgccaagta tggcactatg atcggcgaag ggctcgagac tataaaatat      540
ctcgggcttt tactgcgcag actgcgtgag ggttaccgcg ctgttaagcg tggcgattta      600
cgtgctcttc gtagggttat ccagtcctac cataatggta agtggaaacc ggctactgct      660
ggtaatctct ggcttgaatt tcgttatggc cttatgcctc tcttttatga catcagagat      720
gtcatgttag actggcagaa ccgtcatgat aagattcaac gcctccttcg gtttttctgtt     780 ggtcacggcg aggattacgt tgtcgaattc gacaatctgt accctgccgt tgcttacttt      840
aaactgaaag gggagattac actcgaacgc cgtcatcgtc atggcatatc ttacgctaac      900
cgcgaaggat atgctgtttt cgacaacggt tcccttcggc ctgtgtccga ttggaaggag      960
cttgccactg cattcatcaa tccgcatgaa gttgcttggg agttaactcc ctacagcttc     1020
gttgttgatt ggttcttgaa tgttggtgac atacttgctc aacaaggtca gctatatcat     1080
aatatcgata ttgtagacgg ctttgacaga cgtgacatcc ggctcaaatc tttcaccata     1140
aaaggtgaac gaaatgggcg gcctgttaac gtttctgcta gcctgtctgc tgtcgattta     1200
ttttacagcc gactccatac gagcaatctt ccgttcgcta cactagatct tgatactacc     1260
tttagttcgt ttaaacacgt tcttgatagt atcttttttat taacccaacg cgtaaagcgt    1320
tgaaactttg ggtcaatttg atcatggcaa aattagagac tgttacttta ggtaacatcg     1380
ggaaagatgg aaaacaaact ctggtcctca atccgcgtgg ggtaaatccc actaacggcg     1440
ttgcctcgct ttcacaagcg ggtgcagttc ctgcgctgga gaagcgtgtt accgtttcgg     1500
tatctcagcc ttctcgcaat cgtaagaact acaaggtcca ggttaagatc cagaacccga     1560
ccgcttgcac tgcaaacggt tcttgtgacc catccgttac tcgccaggca tatgctgacg     1620
tgaccttttc gttcacgcag tatagtaccg atgaggaacg agcttttgtt cgtacagagc     1680
ttgctgctct gctcgctagt cctctgctga tcgatgctat tgatcagctg aacccagcgt     1740
attgaacact gctcattgcc ggtggtggct cagggtcaaa acccgatccg gttattccgg     1800
atccaccgat tgatccgccg ccagggacag gtaagtatac ctgtcccttc gcaatttggt     1860
ccctagagga ggtttacgag cctcctacta agaaccgacc gtggcctatc tataatgctg     1920
ttgaactcca gcctcgcgaa tttgatgttg ccctcaaaga tcttttgggc aatacaaagt     1980
ggcgtgattg ggattctcgg cttagttata ccacgttccg cggttgccgt ggcaatggtt     2040
atattgacct tgatgcgact tatcttgcta ctgatcaggc tatgcgtgat cagaagtatg     2100
atattcgcga gggcaagaaa cctggtgctt tcggtaacat tgagcgattc atttatctta     2160
agtcgataaa tgcttattgc tctcttagcg atattgcggc ctatcacgcc gatggcgtga     2220
tagttggctt ttggcgcgat ccatccagtg gtggtgccat accgtttgac ttcactaagt     2280
ttgataagac taaatgtcct attcaagccg tgatagtcgt tcctcgtgct tagtaactaa     2340
ggatgaaatg catgtctaag acagcatctt cgcgtaactc tctcagcgca caattgcgcc     2400
gagccgcgaa cacaagaatt gaggttgaag gtaacctcgc actttccatt gccaacgatt     2460
tactgttggc ctatggtcag tcgccatttta actctgaggc tgagtgtatt tcattcagcc     2520
cgagattcga cgggaccccg gatgacttta ggataaatta tcttaaagcc gagatcatgt     2580
cgaagtatga cgacttcagc ctaggtattg ataccgaagc tgttgcctgg gagaagttcc     2640
tggcagcaga ggctgaatgt gctttaacga acgctcgtct ctataggcct gactacagtg     2700
```

-continued

```
aggatttcaa tttctcactg ggcgagtcat gtatacacat ggctcgtaga aaaatagcca    2760
agctaatagg agatgttccg tccgttgagg gtatgttgcg tcactgccga ttttctggcg    2820
gtgctacaac aacgaataac cgttcgtacg gtcatccgtc cttcaagttt gcgcttccgc    2880
aagcgtgtac gcctcgggct ttgaagtatg ttttagctct cagagcttct acacatttcg    2940
atatcagaat ttctgatatt agcccttta ataaagcagt tactgtacct aagaacagta    3000
agacagatcg ttgtattgct atcgaacctg gttggaatat gttttttccaa ctgggtatcg   3060 gtggcattct acgcgatcgg ttgcgttgct ggggtatcga tctgaatgat cagacgataa    3120
atcagcgccg cgctcacgaa ggctccgtta ctaataactt agcaacggtt gatctctcag    3180
cggcaagcga ttctatatct cttgccctct gtgagctctt attgccccca ggctggtttg    3240
aggttcttat ggacctcaga tcacctaagg ggcgattgcc tgacggtagt gttgttacct    3300
acgagaagat ttcttctatg ggtaacggtt acacattcga gctcgagtcg cttattttg    3360 cttctctcgc tcgttccgtt tgtgagatac tggacttaga ctcgtctgag gtcactgttt    3420
acggagacga tattatttta ccgtcctgtg cagtccctgc cctccgggaa gtttttaagt    3480
atgttggttt tacgaccaat actaaaaaga cttttttccga ggggccgttc agagagtcgt    3540
gcggcaagca ctactattct ggcgtagatg ttactcccct ttacatacgt caccgtatag    3600
tgagtcctgc cgatttaata ctggttttga ataacctata tcggtgggcc acaattgacg    3660
gcgtatggga tcctagggcc cattctgtgt acctcaagta tcgtaagttg ctgcctaaac    3720
agctgcaacg taatactata cctgatggtt acggtgatgg tgccctcgtc ggatcggtcc    3780
taatcaatcc tttcgcgaaa aaccgcgggt ggatccggta cgtaccggtg attacggacc    3840
atacaaggga ccgagagcgc gctgagttgg ggtcgtatct ctacgacctc ttctcgcgtt    3900
gtctctcgga aagtaacgat gggttgcctc ttaggggtcc atcgggttgc gattctgcgg    3960
atctatttgc catcgatcag cttatctgta ggagtaatcc tacgaagata agcaggtcta    4020
ccggcaaatt cgatatacag tatatcgcgt gcagtagccg tgttctggca ccctacgggg    4080
tcttccagga cacgaaggtt gcgtctctac acgaggcgta acctgggagg gcgccaatat    4140
ggcgcctaat tgtgaataaa ttatcacaat tactcttacg agtgagaggg ggatctgctt    4200
tgccctctct cctcccgggg gatccactag ttctaggtac tcgggcagcg ttgggtcctg    4260
gccacgggtg cgcatgatcg tgctcctgtc gttgaggacc cggctaggct ggcggggttg    4320
ccttactggt tagcagaatg aatcaccgat acgcgagcga acgtgaagcg actgctgctg    4380
caaaacgtct gcgacctgag caacaacatg aatggtcttc ggtttccgtg tttcgtaaag    4440
tctggaaacg cggaagtcag cgccctgcac cattatgttc cggatctgca tcgcaggatg    4500
ctgctggcta ccctgtggaa cacctacatc tgtattaacg aagcgctggc attgaccctg    4560
agtgattttt ctctggtccc gccgcatcca taccgccagt tgtttaccct cacaacgttc    4620
cagtaaccgg gcatgttcat catcagtaac ccgtatcgtg agcatcctct ctcgtttcat    4680
cggtatcatt accccatga acagaaattc ccccttacac ggaggcatca agtgaccaaa    4740
caggaaaaaa ccgcccttaa catggcccgc tttatcagaa gccagacatt aacgcttctg    4800
gagaaactca acgagctgga cgcggatgaa caggcagaca tctgtgaatc gcttcacgac    4860
cacgctgatg agctttaccg cagctgcctc gcgcgtttcg gtgatgacgg tgaaaacctc    4920
tgacacatgc agctcccgga gacggtcaca gcttgtctgt aagcggatgc cgggagcaga    4980
caagcccgtc agggcgcgtc agcgggtgtt ggcgggtgtc ggggcgcagc catgacccag    5040
tcacgtagcg atagcggagt gtatactggc ttaactatgc ggcatcagag cagattgtac    5100
```

```
tgagagtgca ccatatgcgg tgtgaaatac cgcacagatg cgtaaggaga aaataccgca   5160
tcaggcgctc ttccgcttcc tcgctcactg actcgctgcg ctcggtcgtt cggctgcggc   5220
gagcggtatc agctcactca aaggcggtaa tacggttatc cacagaatca ggggataacg   5280
caggaaagaa catgtgagca aaaggccagc aaaaggccag gaaccgtaaa aaggccgcgt   5340
tgctggcgtt tttccatagg ctccgccccc ctgacgagca tcacaaaaat cgacgctcaa   5400
gtcagaggtg gcgaaacccg acaggactat aaagatacca ggcgtttccc cctggaagct   5460
ccctcgtgcg ctctcctgtt ccgaccctgc cgcttaccgg atacctgtcc gcctttctcc   5520
cttcgggaag cgtggcgctt tctcatagct cacgctgtag gtatctcagt tcggtgtagg   5580
tcgttcgctc caagctgggc tgtgtgcacg aaccccccgt tcagcccgac cgctgcgcct   5640
tatccggtaa ctatcgtctt gagtccaacc cggtaagaca cgacttatcg ccactggcag   5700
cagccactgg taacaggatt agcagagcga ggtatgtagg cggtgctaca gagttcttga   5760
agtggtggcc taactacggc tacactagaa ggacagtatt tggtatctgc gctctgctga   5820
agccagttac cttcggaaaa agagttggta gctcttgatc cggcaaacaa accaccgctg   5880
gtagcggtgg tttttttgtt tgcaagcagc agattacgcg cagaaaaaaa ggatctcaag   5940
aagatccttt gatcttttct acgggtctg acgctcagtg aacgaaaac tcacgttaag   6000 ggattttggt catgagatta tcaaaaagga tcttcaccta gatccttta aattaaaaat   6060 gaagttttaa atcaatctaa agtatatatg agtaaacttg gtctgacagt taccaatgct   6120
taatcagtga ggcacctatc tcagcgatct gtctatttcg ttcatccata gttgcctgac   6180
tccccgtcgt gtagataact acgatacggg agggcttacc atctggcccc agtgctgcaa   6240
tgataccgcg agacccacgc tcaccggctc cagatttatc agcaataaac cagccagccg   6300
gaagggccga gcgcagaagt ggtcctgcaa ctttatccgc ctccatccag tctattaatt   6360
gttgccggga agctagagta agtagttcgc cagttaatag tttgcgcaac gttgttgcca   6420
ttgctgcagg catcgtggtg tcacgctcgt cgtttggtat ggcttcattc agctccggtt   6480
cccaacgatc aaggcgagtt acatgatccc ccatgttgtg caaaaaagcg gttagctcct   6540
tcggtcctcc gatcgttgtc agaagtaagt tggccgcagt gttatcactc atggttatgg   6600
cagcactgca taattctctt actgtcatgc catccgtaag atgcttttct gtgactggtg   6660
agtactcaac caagtcattc tgagaatagt gtatgcggcg accgagttgc tcttgcccgg   6720
cgtcaacacg ggataatacc gcgccacata gcagaacttt aaaagtgctc atcattggaa   6780
aacgttcttc ggggcgaaaa ctctcaagga tcttaccgct gttgagatcc agttcgatgt   6840
aacccactcg tgcacccaac tgatcttcag catcttttac tttcaccagc gtttctgggt   6900
gagcaaaaac aggaaggcaa aatgccgcaa aaaagggaat aagggcgaca cggaaatgtt   6960
gaatactcat actcttcctt tttcaatatt attgaagcat ttatcagggt tattgtctca   7020
tgagcggata catatttgaa tgtatttaga aaaataaaca aataggggtt ccgcgcacat   7080
ttccccgaaa agtgccacct gacgtctaag aaaccattat tatcatgaca ttaacctata   7140
aaaataggcg tatcacgagg ccctttcgtc ttcaagaatt ggcgaacgtg gcgagaaagg   7200
aagggaagaa agcgaaagga gcgggcgcta gggcgctggc aagtgtagcg gtcacgctgc   7260
gcgtaaccac cacacccgcc gcgcttaatg cgccgctaca gggcgcgtcc cattcgccat   7320
tcaggctacg caactgttgg gaagggcgat cggtgcgggc ctcttcgcta ttacgccagc   7380
tggcgaaggg gggatgtgct gcaaggcgat taagttgggt aacgccaggg ttttcccagt   7440
```

```
cacgacgttg taaaacgacg gccagtgaat tgtaatacga ctcactata                 7489

<210> SEQ ID NO 6
<211> LENGTH: 1716
<212> TYPE: DNA
<213> ORGANISM: hepatitis C virus
<220> FEATURE:
<221> NAME/KEY: misc_feature
<222> LOCATION: (1)..(176)
<223> OTHER INFORMATION: DNA sequence of the hepatitis C virus RNA
      dependent RNA polymerase

<400> SEQUENCE: 6
tctatgtcgt actcttggac cggcgccctg ataacaccgt gtagtgctga ggaggagaaa      60
ctgcccatca gcccactcag caactccttg ctgagacatc ataacctagt ctattcaacg     120
tcgtctagaa gcgcttctca gcgtcagagg aaggttacct tcgacagact gcaggtgctc     180
gacgaccatt acaagactgt attaaaggag gtaaaggagc gagcgtctag ggtaaaggct     240
cgcatgctca ccatcgagga agcgtgcgcg ctcgtccctc ctcactctgc ccggtcgaaa     300
ttcgggtata gtgcgaagga cgttcgctcc ttgtctagca gggccattaa ccagatccgc     360
tccgtctggg aggacttgct agaagacacc acaactccaa ttccaaccac catcatggcg     420
aagaacgagg tgttttgtgt ggaccccgct aaggggggcc gcaagcccgc tcgccttatc     480
gtgtaccctg acctgggggt tcgtgtctgc gagaaacgcg ccctatatga cgtgatacag     540
aagttggcaa ttgagacgat tggttctgct tacggattcc aatactcgcc tcaacagcgg     600
gtcgaacgtc tgctcaagat gtggacctca agaaaaccc ccttggggtt ctcgtatgac     660
acccgctgct ttgactcaac tgtcactgaa caggacatca gggtggaaga ggagatatac     720
caatgctgca accttgaacc ggaggccagg aaagtgatct cctccctcac ggagcggctt     780
tactgcgggg gccctatgtt caacagcaag ggggctcagt gtggtgaccg tcgttgccgt     840
gccagtggag ttttgcctac cagctttggc aatacaatca cttgttacat caaagccaca     900
gcggctgcga acgcgcagg cctccgggac ccggactttc ttgtctgcgg agatgatctg     960
gtcgtggtgg ccgagagtga cggcgtcgat gaggatgggg cagccctgag agccttcacg    1020
gaggctatga ccaggtattc tgctccaccc ggagatgctc cacagcccac ctacgacctt    1080
gagctcatca catcttgctc ctccaacgtc tccgtggcac gggacgacaa ggggaggagg    1140
tactattacc tcacccgtga tgccaccact cccctagccc gtgcggcttg ggaaacagct    1200
cgtcacactc cagttaactc ctggttaggt aacatcatca tgtacgcgcc taccatctgg    1260
gtgcgcatgg taatgatgac acactttttc tccatactcc aatcccagga gatacttgat    1320
cgaccccttg acttcgaaat gtacgggggcc acttactcgg tcacgccgct ggatttacca    1380
gcaatcattg aaagactcca tggtctaagc gcgttcacgc tccacagtta ctctccagta    1440
gagctcaata gggtcgcggg gacactcagg aagctgggt gccccccct acgagcttgg    1500 agacatcggg cacgagcagg gcgcgctaag cttatcgccc agggagggaa ggccaaaata    1560
tgcggccttt atctctttaa ttgggcggta cgcaccaaga ccaaactcac tccgctgcca    1620
cgcgctggcc agttggattt atccatctgg tttacggttg gcgtcggcgg gaacgacatt    1680
tatcacagcg tgtcgcgtgc ccgaacccgc tattag                              1716

<210> SEQ ID NO 7
<211> LENGTH: 65
<212> TYPE: DNA
<213> ORGANISM: Artificial
<220> FEATURE:
```

<223> OTHER INFORMATION: primer N5266

<400> SEQUENCE: 7
gcgcgaatac gactcactat agagggacaa accgccatgg ccgaggtgag gcttcttgag      60
tctgg      65

<210> SEQ ID NO 8
<211> LENGTH: 58
<212> TYPE: DNA
<213> ORGANISM: Artificial
<220> FEATURE:
<223> OTHER INFORMATION: primer N5267

<400> SEQUENCE: 8
catcatcatc atctttataa tctgcggccg cacactctcc cctgttgaag ctcttgac      58

<210> SEQ ID NO 9
<211> LENGTH: 57
<212> TYPE: DNA
<213> ORGANISM: Artificial
<220> FEATURE:
<223> OTHER INFORMATION: primer N5268

<400> SEQUENCE: 9
cccctgttga agctcttgac aatgggtgaa gttgatgtct tgtgagtggc ctcacag      57

<210> SEQ ID NO 10
<211> LENGTH: 46
<212> TYPE: DNA
<213> ORGANISM: Artificial
<220> FEATURE:
<223> OTHER INFORMATION: primer N5269

<400> SEQUENCE: 10
cttgtgagtg gcctcacagg tatagctgtt atgtcgttca tactcg      46

<210> SEQ ID NO 11
<211> LENGTH: 55
<212> TYPE: DNA
<213> ORGANISM: Artificial
<220> FEATURE:
<223> OTHER INFORMATION: primer N5343

<400> SEQUENCE: 11
accatgatta cgccaagctc taatacgact cactataggg aaagctcgct tgttc      55

<210> SEQ ID NO 12
<211> LENGTH: 60
<212> TYPE: DNA
<213> ORGANISM: Artificial
<220> FEATURE:
<223> OTHER INFORMATION: primer N5344

<400> SEQUENCE: 12
agggaaagct cgcttgttct ttttgcagaa gctcagaata acgctcaac tttggccacc      60

<210> SEQ ID NO 13
<211> LENGTH: 39
<212> TYPE: DNA
<213> ORGANISM: Artificial
<220> FEATURE:
<223> OTHER INFORMATION: primer N5353

<400> SEQUENCE: 13
tttataatct gcggccgccg cctcgtgtag agacgcaac      39

<210> SEQ ID NO 14
<211> LENGTH: 48
<212> TYPE: DNA
<213> ORGANISM: Artificial
<220> FEATURE:
<223> OTHER INFORMATION: primer N5354

<400> SEQUENCE: 14
ttactcgcgg cccagccggc catggccatg tctaagacag catcttcg        48

<210> SEQ ID NO 15
<211> LENGTH: 60
<212> TYPE: DNA
<213> ORGANISM: Artificial
<220> FEATURE:
<223> OTHER INFORMATION: primer N5355

<400> SEQUENCE: 15
gcagctaata cgactcacta taggaacaga ccaccatgga cgtggcccag cctgctgtgg        60

<210> SEQ ID NO 16
<211> LENGTH: 50
<212> TYPE: DNA
<213> ORGANISM: Artificial
<220> FEATURE:
<223> OTHER INFORMATION: primer N5384

<400> SEQUENCE: 16
aaacgctcaa ctttggccac catggatgtg aagcttcagg agtctgggcc        50

<210> SEQ ID NO 17
<211> LENGTH: 51
<212> TYPE: DNA
<213> ORGANISM: Artificial
<220> FEATURE:
<223> OTHER INFORMATION: primer N5385

<400> SEQUENCE: 17
gcccttgggc cgggagatgg tctgcttcag tggcgagggc aggtctgtgt g        51

<210> SEQ ID NO 18
<211> LENGTH: 49
<212> TYPE: DNA
<213> ORGANISM: Artificial
<220> FEATURE:
<223> OTHER INFORMATION: primer N5386

<400> SEQUENCE: 18
cgagggcagg tctgtgtggg tcacggtgca cgtgaacctc tccccggag        49

<210> SEQ ID NO 19
<211> LENGTH: 51
<212> TYPE: DNA
<213> ORGANISM: Artificial
<220> FEATURE:
<223> OTHER INFORMATION: primer N5387

<400> SEQUENCE: 19
cgtgaacctc tccccggagt tccagtcatc ctcgcagatg ctggcctcac c        51

<210> SEQ ID NO 20
<211> LENGTH: 65
<212> TYPE: DNA
<213> ORGANISM: Artificial
<220> FEATURE:

-continued

```
<223> OTHER INFORMATION: primer N5517

<400> SEQUENCE: 20
gcgcgaatac gactcactat agagggacaa accgccatgg ccgatgtgaa gcttcaggag    60
tcagg                                                                65

<210> SEQ ID NO 21
<211> LENGTH: 60
<212> TYPE: DNA
<213> ORGANISM: Artificial
<220> FEATURE:
<223> OTHER INFORMATION: primer N5659

<400> SEQUENCE: 21
gcagctaata cgactcacta taggaacaga ccaccatgga cgtggcccag cctgctgtgg    60

<210> SEQ ID NO 22
<211> LENGTH: 54
<212> TYPE: DNA
<213> ORGANISM: Artificial
<220> FEATURE:
<223> OTHER INFORMATION: primer N5904

<400> SEQUENCE: 22
taatacgact cactataggg aaagggtttc tccgatccgg gaacatagga tacc          54

<210> SEQ ID NO 23
<211> LENGTH: 61
<212> TYPE: DNA
<213> ORGANISM: Artificial
<220> FEATURE:
<223> OTHER INFORMATION: primer N5909

<400> SEQUENCE: 23
tgaggtatcc tatgttcccg gatcggagaa acccacactc tccctgttg aagctcttga    60 c                                                                    61

<210> SEQ ID NO 24
<211> LENGTH: 56
<212> TYPE: DNA
<213> ORGANISM: Artificial
<220> FEATURE:
<223> OTHER INFORMATION: primer N5910

<400> SEQUENCE: 24
ccgggaacat aggatacctc aaccaccatg gccgaggtga ggcttcttga gtctgg        56

<210> SEQ ID NO 25
<211> LENGTH: 23
<212> TYPE: DNA
<213> ORGANISM: Artificial
<220> FEATURE:
<223> OTHER INFORMATION: primer

<400> SEQUENCE: 25
gaggtgaggc ttcttgagtc tgg                                            23

<210> SEQ ID NO 26
<211> LENGTH: 22
<212> TYPE: DNA
<213> ORGANISM: Artificial
<220> FEATURE:
<223> OTHER INFORMATION: primer

<400> SEQUENCE: 26
```

```
gctgttatgt cgttcatact cg                                    22

<210> SEQ ID NO 27
<211> LENGTH: 28
<212> TYPE: RNA
<213> ORGANISM: Artificial
<220> FEATURE:
<223> OTHER INFORMATION: sequence of the stemloop structure for binding
      the replicase

<400> SEQUENCE: 27
gggacacgaa agccccagga accuuucg                              28

<210> SEQ ID NO 28
<211> LENGTH: 23
<212> TYPE: DNA
<213> ORGANISM: Artificial
<220> FEATURE:
<223> OTHER INFORMATION: T7 promoter

<400> SEQUENCE: 28
taatacgact cactataggg aga                                   23

<210> SEQ ID NO 29
<211> LENGTH: 8
<212> TYPE: PRT
<213> ORGANISM: Artificial
<220> FEATURE:
<223> OTHER INFORMATION: octapeptide "FLAG" epitope

<400> SEQUENCE: 29

Asp Tyr Lys Asp Asp Asp Asp Lys
1               5

<210> SEQ ID NO 30
<211> LENGTH: 42
<212> TYPE: DNA
<213> ORGANISM: Artificial
<220> FEATURE:
<223> OTHER INFORMATION: primer # 5352

<400> SEQUENCE: 30
tctgcagaat tcgccgccac catgtctaag acagcatctt cg              42

<210> SEQ ID NO 31
<211> LENGTH: 39
<212> TYPE: DNA
<213> ORGANISM: Artificial
<220> FEATURE:
<223> OTHER INFORMATION: primer # 5350

<400> SEQUENCE: 31
tttataarct gcggccgctt acgcctcgtg tagagacgc                  39

<210> SEQ ID NO 32
<211> LENGTH: 42
<212> TYPE: DNA
<213> ORGANISM: Artificial
<220> FEATURE:
<223> OTHER INFORMATION: sequence of DNA dependent RNA polymerase
      promoter

<400> SEQUENCE: 32
gcgcgaatac gactcactat agagggacaa accgccatgg cc              42
```

```
<210> SEQ ID NO 33
<211> LENGTH: 41
<212> TYPE: DNA
<213> ORGANISM: Artificial
<220> FEATURE:
<223> OTHER INFORMATION: sequence of DNA dependent RNA polymerase
      promoter

<400> SEQUENCE: 33
gcagctaata cgactcacta taggaacaga ccaccatggc c                    41

<210> SEQ ID NO 34
<211> LENGTH: 20
<212> TYPE: PRT
<213> ORGANISM: Artificial
<220> FEATURE:
<223> OTHER INFORMATION: linker

<400> SEQUENCE: 34

Gly Ser Gly Ser Gly His His His His His His His His His Asp
1               5                   10                  15

Asp Asp Asp Lys
            20

<210> SEQ ID NO 35
<211> LENGTH: 42
<212> TYPE: DNA
<213> ORGANISM: Artificial
<220> FEATURE:
<223> OTHER INFORMATION: primer

<400> SEQUENCE: 35
gtggtggaat tcgccgccac ctctatgtcg tactcttgga cc                   42

<210> SEQ ID NO 36
<211> LENGTH: 39
<212> TYPE: DNA
<213> ORGANISM: Artificial
<220> FEATURE:
<223> OTHER INFORMATION: primer

<400> SEQUENCE: 36
gcacgggctt gggcgataat ccgccggcga gctcagatc                       39

<210> SEQ ID NO 37
<211> LENGTH: 54
<212> TYPE: RNA
<213> ORGANISM: Unknown
<220> FEATURE:
<223> OTHER INFORMATION: sequence of RNA fragment that forms stemloop
      structure

<400> SEQUENCE: 37 ggggguuuccg ggaacauagg auaccucauc ucuauaguga gucguauuuu ccca     54

<210> SEQ ID NO 38
<211> LENGTH: 57
<212> TYPE: RNA
<213> ORGANISM: Unknown
<220> FEATURE:
<223> OTHER INFORMATION: sequence of RNA fragment that forms stemloop
      structure

<400> SEQUENCE: 38
gcgcgaauac gacucaucau agagggacaa accaugaggu caaacucgag agucagg   57
```